(12) United States Patent  
Yu et al.

(10) Patent No.: US 12,070,673 B2  
(45) Date of Patent: Aug. 27, 2024

(54) INTELLIGENT VOICE PLAYING METHOD AND DEVICE

(71) Applicant: Huawei Technologies Co., Ltd., Shenzhen (CN)

(72) Inventors: Xindi Yu, Shenzhen (CN); Hang Liu, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 73 days.

(21) Appl. No.: 17/634,601

(22) PCT Filed: Aug. 21, 2020

(86) PCT No.: PCT/CN2020/110623  
§ 371 (c)(1),  
(2) Date: Feb. 11, 2022

(87) PCT Pub. No.: WO2021/036954  
PCT Pub. Date: Mar. 4, 2021

(65) Prior Publication Data  
US 2022/0323848 A1 Oct. 13, 2022

(30) Foreign Application Priority Data  
Aug. 30, 2019 (CN) .......... 201910818708.0

(51) Int. Cl.  
*A63B 71/06* (2006.01)  
*G06V 10/75* (2022.01)  
*G06V 40/20* (2022.01)

(52) U.S. Cl.  
CPC ........ *A63B 71/0622* (2013.01); *G06V 10/751* (2022.01); *G06V 40/23* (2022.01); *A63B 2071/063* (2013.01); *A63B 2071/0638* (2013.01); *A63B 2071/0694* (2013.01); *A63B 2220/05* (2013.01); *A63B 2220/807* (2013.01)

(58) Field of Classification Search  
CPC ... G06V 40/23; G06V 10/751; A63B 71/0622  
See application file for complete search history.

(56) References Cited

U.S. PATENT DOCUMENTS

| | | | |
|---|---|---|---|
| 2011/0294586 A1 | 12/2011 | Cho et al. | |
| 2011/0307927 A1 | 12/2011 | Nakano et al. | |
| 2014/0228985 A1 | 8/2014 | Elliott et al. | |
| 2015/0347717 A1 | 12/2015 | Dalal et al. | |

(Continued)

FOREIGN PATENT DOCUMENTS

| | | |
|---|---|---|
| CN | 101202994 A | 6/2008 |
| CN | 101810923 A | 8/2010 |

(Continued)

*Primary Examiner* — Kesha Frisby  
(74) *Attorney, Agent, or Firm* — Conley Rose, P.C.

(57) ABSTRACT

An intelligent voice playing method includes displaying, by an electronic device, an interface of a first application, where the first application is used by a user to perform exercise training; capturing an image of a training action of the user; playing a video of a standard action, and displaying the image of the training action of the user; determining a plurality of to-be-selected voices triggered by a first action unit in the training action of the user, where the first action unit is one training action or a part of one training action; and selecting a voice from the to-be-selected voices for playing.

20 Claims, 15 Drawing Sheets

(56) References Cited

U.S. PATENT DOCUMENTS

| | | |
|---|---|---|
| 2018/0315247 A1 | 11/2018 | Van Andel |
| 2018/0339195 A1 | 11/2018 | Bernotas |
| 2019/0077007 A1 | 3/2019 | Mallinson |
| 2019/0201744 A1 | 7/2019 | Shen |

FOREIGN PATENT DOCUMENTS

| | | |
|---|---|---|
| CN | 102365115 A | 2/2012 |
| CN | 103050138 A | 4/2013 |
| CN | 105148479 A | 12/2015 |
| CN | 106110627 A | 11/2016 |
| CN | 106139564 A | 11/2016 |
| CN | 103413018 B | 4/2017 |
| CN | 106730760 A | 5/2017 |
| CN | 106984027 A | 7/2017 |
| CN | 107551521 A | 1/2018 |
| CN | 108601133 A | 9/2018 |
| CN | 108654061 A | 10/2018 |
| CN | 108694240 A | 10/2018 |
| CN | 108853946 A | 11/2018 |
| CN | 109011508 A | 12/2018 |
| CN | 109087694 A | 12/2018 |
| CN | 109144247 A | 1/2019 |
| CN | 109165560 A | 1/2019 |
| CN | 109407829 A | 3/2019 |
| CN | 109745163 A | 5/2019 |
| CN | 110052013 A | 7/2019 |
| CN | 110110647 A | 8/2019 |
| CN | 110170159 A | 8/2019 |
| CN | 111095150 A | 5/2020 |
| CN | 210864619 U | 6/2020 |
| JP | 2004024627 A | 1/2004 |
| JP | 2010137097 A | 6/2010 |
| KR | 20180103280 A | 9/2018 |

"Please stand in front of the screen"

🔊 "Please laterally flex to the hand holding the dumbbell"

INTELLIGENT VOICE PLAYING METHOD AND DEVICE

CROSS-REFERENCE TO RELATED APPLICATIONS

This is a U.S. National Stage of International Patent Application No. PCT/CN2020/110623 filed on Aug. 21, 2020, which claims priority to Chinese Patent Application No. 201910818708.0 filed on Aug. 30, 2019, both of which are hereby incorporated by reference in their entireties.

TECHNICAL FIELD

Embodiments of this application relate to the field of electronic technologies, and in particular, to an intelligent voice playing method and a device.

BACKGROUND

In recent years, with increasing fitness demands and enhanced fitness consciousness, fitness enthusiasts gradually increase. As life tempo accelerates, many fitness enthusiasts often do not have time to go to a gym for dedicated fitness training. A smart fitness solution based on image processing enables users to get professional fitness instruction at home.

According to a smart fitness solution in a conventional technology, an video of a standard action of a coach is played on a large-screen device, to provide professional action instruction for a user, and the user performs training with reference to the standard action of the coach. In addition, the large-screen device may further play a preset set of voices in cooperation with the coach video, to assist the coach video in instructing the user to perform fitness training.

In the smart fitness solution, the large-screen device mechanically repeatedly plays the same set of preset fixed voices, leading to relatively monotonous and uninteresting voice playing. Especially, when the user performs training with the solution a plurality of times, the user hears the same voices repeatedly played each time, which easily causes the user to feel bored and lose interest. Therefore, user experience is relatively poor.

SUMMARY

Embodiments of this application provide an intelligent voice playing method and a device, so that different voices can be played in real time for a current training state and training action of a user, to provide the user with real-time voice feedback and real-time guidance for action improvement. In addition, voice content is abundant and diversified, and user experience is relatively good.

To achieve the foregoing objectives, the following technical solutions are used in the embodiments of this application.

According to one aspect, an embodiment of this application provides a voice playing method. The method includes: An electronic device displays an interface of a first application. The first application is used by a user to perform exercise training. The electronic device captures an image of a training action of the user. The electronic device plays an video of a standard action, and displays the image of the training action of the user. The electronic device determines to-be-selected voices triggered by a first action unit in the training action of the user. The to-be-selected voices include a plurality of voices. The first action unit is one training action or a part of one training action. The electronic device selects a voice from the to-be-selected voices for playing.

In this solution, the electronic device can determine, in real time for a current action unit of the user, a plurality of to-be-selected voices that match an exercise state of the user, and select different voices from the to-be-selected voices for playing, to provide real-time voice feedback to the user. In addition, played voice content is abundant and diversified and not easily repeated, and user experience is relatively good.

In a possible design, the to-be-selected voices include a main flow voice and a non-main flow voice. The main flow voice is used to enable the exercise training to be normally performed. The non-main flow voice includes one or more of an action improvement voice, an action evaluation voice, or a training tempo voice. The main flow voice is a high-priority voice, and the non-main flow voice is a low-priority voice. That the electronic device selects a voice from the to-be-selected voices for playing includes: The electronic device selects a voice from the to-be-selected voices based on priorities of the voices for playing.

In other words, voices that can be played by the electronic device include a plurality of types. When the user performs exercise training according to a coach video, the electronic device may play, in real time based on priorities of the voices, a plurality of different types of voices for a current exercise state and exercise action of the user, so that to-be-played voice content is abundant and diversified, which can avoid a monotonous feeling caused by playing a fixed set of voices, increase training interest of the user, and improve usage experience of the user.

In another possible design, the to-be-selected voices include at least one high-priority main flow voice, and that the electronic device selects a voice from the to-be-selected voices based on priorities of the voices for playing includes: The electronic device separately plays each high-priority main flow voice in the to-be-selected voices.

Because the main flow voice is used to ensure that the exercise training is normally performed, the main flow voice is relatively important and has a high priority, and the electronic device may sequentially play each main flow voice.

In another possible design, when the electronic device plays each main flow voice, the method further includes: The electronic device stops playing the video of the standard action. The electronic device displays first graphic and text information. The first graphic and text information corresponds to the main flow voice. After the electronic device detects that the user adjusts to a state required by the first graphic and text information, the electronic device displays a completion identifier on the first graphic and text information. Then the electronic device stops displaying the first graphic and text information. The electronic device resumes playing the video of the standard action.

The first graphic and text information may be graphic and text information in a form of a task card. When playing the main flow voice, the electronic device may display the first graphic and text information and suspend a progress of the exercise training. After the user performs a corresponding adjustment according to the main flow voice or the first graphic and text information, the electronic device may stop displaying the first graphic and text information and continue subsequent exercise training.

In another possible design, in addition to the at least one main flow voice, the to-be-selected voice may further include at least one non-main flow voice.

In other words, if the electronic device determines that the to-be-selected voices triggered by the first action unit include at least one main flow voice and at least one non-main flow voice, the electronic device plays the at least one high-priority main flow voice.

In another possible design, the to-be-selected voices include a plurality of low-priority non-main flow voices. That the electronic device selects a voice from the to-be-selected voices based on priorities of the voices for playing includes: The electronic device selects a first target voice from the plurality of low-priority non-main flow voices. The electronic device plays the first target voice.

In this solution, if the electronic device determines that the to-be-selected voices triggered by the first action unit include at least one low-priority non-main flow voice and include no main flow voice, the electronic device selects a voice from the at least one non-main flow voice for playing, to avoid a problem, caused by playing the plurality of voices corresponding to the action unit, of mismatch between voice playing and a subsequent action unit.

In another possible design, the first target voice is the first triggered voice in the plurality of non-main flow voices.

In other words, the electronic device selects the first triggered voice based on a triggering sequence for playing.

In another possible design, the first target voice is a first action improvement voice for a first error in the action unit. That the electronic device plays the first target voice includes: if the electronic device has not played, in the current exercise training, the first action improvement voice for a training action of a type to which the action unit belongs, the electronic device plays the first action improvement voice. The method further includes: if the electronic device has played, in the current exercise training, the first action improvement voice for the training action of the type to which the action unit belongs, the electronic device plays a key action point for the first error; or the electronic device selects a second target voice from other non-main flow voices other than the first action improvement voice.

In this solution, if that voice selected by the electronic device from the to-be-selected voices is an action improvement voice and the action improvement voice has been played, the electronic device does not play the action improvement voice, to avoid a problem of relatively poor user experience caused by same and frequent voice improvement prompts for a same error.

In another possible design, when the electronic device plays the first action improvement voice, the method further includes: The electronic device displays second graphic and text information. The second graphic and text information corresponds to the first action improvement voice. After the electronic device detects that the user adjusts the training action to a state required by the second graphic and text information, the electronic device displays a completion identifier on the second graphic and text information. Then the electronic device stops displaying the second graphic and text information.

The second graphic and text information may be graphic and text information in a form of a task card. When playing the action improvement voice, the electronic device may display the second graphic and text information. After the user performs a corresponding adjustment according to the action improvement voice or the second graphic and text information, the electronic device may stop displaying the second graphic and text information.

In another possible design, the first target voice is a first action evaluation voice, and that the electronic device plays the first target voice includes: If the electronic device determines randomly that a current mode is a first mode, the electronic device plays the first action evaluation voice. The method further includes: If the electronic device determines randomly that the current mode is a second mode, the electronic device does not play the first action evaluation voice.

In other words, after selecting an action evaluation voice from the to-be-selected voices, the electronic device may randomly determine whether to play the action evaluation voice, to avoid frequently and regularly playing the action evaluation voice, and improve uncertainty of playing the action evaluation voice.

In another possible design, the action evaluation voice includes a plurality of levels, each level includes a plurality of voices, the first action evaluation voice is an action evaluation voice at a first level, and that the electronic device plays the first action evaluation voice includes: The electronic device randomly selects a voice from action evaluation voices at the first level for playing.

In this way, when the electronic device determines to play an action evaluation voice, the electronic device may randomly select, for playing, an action evaluation voice from a corpus including a plurality of action evaluation voices, to improve unpredictability and uncertainty of action evaluation content, avoid repeatedly playing an action evaluation voice, and give the user fresh usage experience.

In another possible design, that the electronic device plays the first target voice includes: If the electronic device determines that playing of a voice triggered by another action unit before the first action unit is completed, the electronic device plays the first target voice. The method further includes: If the electronic device determines that the playing of the voice triggered by the another action unit before the first action unit is not completed, the electronic device does not play the first target voice.

In other words, the electronic device plays one voice only after playing of another voice is completed, and voice playing is not interrupted due to voice conflict between different action units.

In another possible design, the to-be-selected voices include one low-priority non-main flow voice, and that the electronic device performs voice playing based on priorities of the voices in the to-be-selected voice includes: The electronic device plays the low-priority first target voice.

In this solution, if the electronic device determines that the to-be-selected voices triggered by the first action unit include one low-priority non-main flow voice, the electronic device plays the voice.

In another possible design, after the electronic device displays the interface of the first application, and before the electronic device determines the to-be-selected voices triggered by the first action unit in the training action of the user, the method further includes: The electronic device determines, based on a progress of the exercise training or a state of the user, that the main flow voice is triggered. The electronic device plays the main flow voice.

In other words, after entering the first application, the electronic device may first determine whether the main flow voice is triggered, and play the triggered main flow voice, to ensure that the exercise training can be normally started.

In another possible design, the action improvement voice is used to guide the user to improve the training action. The action evaluation voice is used to positively evaluate the user for the training action of the user. The training tempo voice is used to prompt the user a progress of the exercise training.

In this way, different types of voices may prompt the exercise training of the user from different aspects and different angles.

In another possible design, the main flow voice includes one or more of a flow-based voice, a position adjustment voice, a stance adjustment voice, or a humanized prompt voice. The action improvement voice includes one or more of a frequency improvement voice, a range improvement voice, or a posture improvement voice.

In other words, each type of voice may further include voice prompts of a plurality of dimensions. In this way, the electronic device may provide voice prompts to the user from different dimensions and angles, so that voice content of voices that can be played may be more abundant, the voice content may be flexible and diversified, and voice prompts are more specific and comprehensive, which can give the user a fresh and interesting feeling, and improve usage experience of the user.

In another possible design, that the electronic device determines to-be-selected voices triggered by a first action unit in the training action of the user includes: The electronic device determines the position adjustment voice, the stance adjustment voice, or the humanized prompt voice in the to-be-selected voices based on a state of the user in a process of performing the first action unit. The electronic device determines the non-main flow voice in the to-be-selected voices based on an action in the first action unit.

In this way, the electronic device may determine, based on action information such as the state of the user in the process of performing the first action unit, a standard degree of an action of the user, and a quantity of actions, the to-be-selected voices triggered by the first action unit.

According to another aspect, an embodiment of this application provides a voice playing apparatus. The apparatus is included in an electronic device. The apparatus has a function of implementing behavior of the electronic device in any method in the foregoing aspect and possible designs. The function may be implemented by hardware, or may be implemented by hardware executing corresponding software. The hardware or the software includes at least one module or unit corresponding to the functions, for example, a display module/unit, a capture module/unit, a determining module/unit, and a playing module/unit.

According to another aspect, an embodiment of this application provides an electronic device, including one or more processors and a memory. The memory stores code. When the code is executed by the electronic device, the electronic device is enabled to perform the voice playing method in any possible design of the foregoing aspect.

According to another aspect, an embodiment of this application provides a computer storage medium, including computer instructions. When the computer instructions are run on a mobile terminal, the mobile terminal is enabled to perform the voice playing method in any possible design of the foregoing aspect.

According to still another aspect, an embodiment of this application provides a computer program product. When the computer program product runs on a computer, the computer is enabled to perform the voice playing method in any possible design of the foregoing aspect.

For beneficial effects corresponding to the foregoing other aspects, refer to the descriptions of the beneficial effects in the method aspects. Details are not described herein again.

DESCRIPTION OF EMBODIMENTS

The following describes the technical solutions in the embodiments of this application with reference to the accompanying drawings in the embodiments of this application. In descriptions of the embodiments of this application, "/" means "or" unless otherwise specified. For example, A/B may represent A or B. In this specification, "and/or" describes only an association relationship for describing associated objects and represents that three relationships may exist. For example, A and/or B may represent the following three cases: Only A exists, both A and B exist, and only B exists. In addition, in the descriptions in the embodiments of this application, "a plurality of" means two or more than two.

The embodiments of this application provide an intelligent voice playing method in an intelligent exercise system, so that when a user performs exercise training according to a coach video, different voices may be played in real time for a current exercise state and exercise action of the user, to provide the user with real-time voice feedback and real-time guidance for action improvement. In addition, voice content is abundant and diversified, and user experience is relatively good.

The exercise system is applied to a scenario in which a user performs AI exercise training with reference to a coach video. For example, the user may perform AI fitness training, AI yoga training, AI bodybuilding operation training, an AI somatosensory game, or other AI exercise training.

Figure 1A:
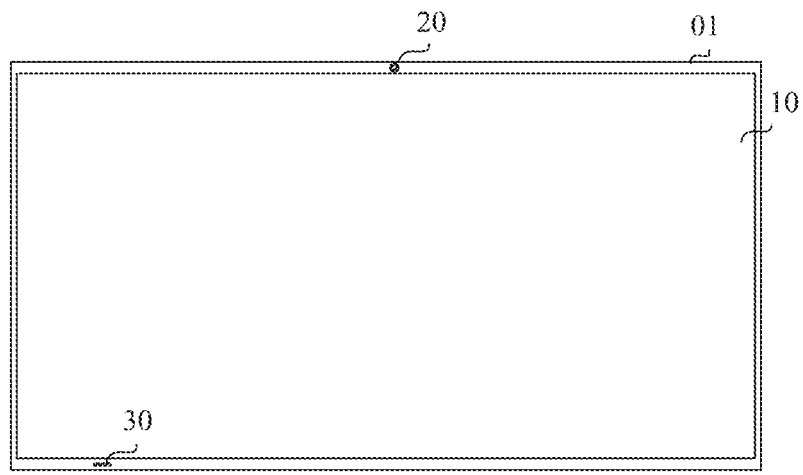
FIG. 1A is a schematic diagram of a structure of an electronic device according to an embodiment of this application.

In some embodiments, referring to FIG. 1A, the intelligent voice playing method provided in the embodiments of this application may be applied to an electronic device 01 having a screen 10, and particularly may be applied to an electronic device 01 having a large screen. The electronic device 01 may further include a camera 20. The camera 20 may be integrated in the electronic device 01, or may be an independent camera outside a main body of the electronic device 01, and connected to the main body of the electronic device 01 in a wired or wireless manner. In addition, the electronic device 01 may further include an audio player 30. The audio player 30 may be integrated into the electronic device 01, for example, may be a speaker or a sound box. Alternatively, the audio player 30 may be an audio playing device connected to the main body of the electronic device 01 in a wired or wireless manner, for example, may be a sound box.

The camera 20 may be configured to capture an image of real-time exercise of a user. The screen 10 of the electronic device 01 may be configured to play a coach video and display the image of the real-time exercise of the user. When the user performs exercise training according to the coach video, the electronic device 01 determines, in real time, to-be-played voices for a current training state and training action of the user, and performs voice playing by using the audio player 30.

For example, the electronic device 01 may be a television, a desktop computer, a tablet computer, a notebook computer, a mobile phone, a smart screen, a projector, an ultra-mobile personal computer (ultra-mobile personal computer, UMPC), a netbook, or an augmented reality (augmented reality, AR)/virtual reality (virtual reality, VR) device, or the like. A specific type of the electronic device 01 is not limited in this embodiment of this application.

Figure 1B:
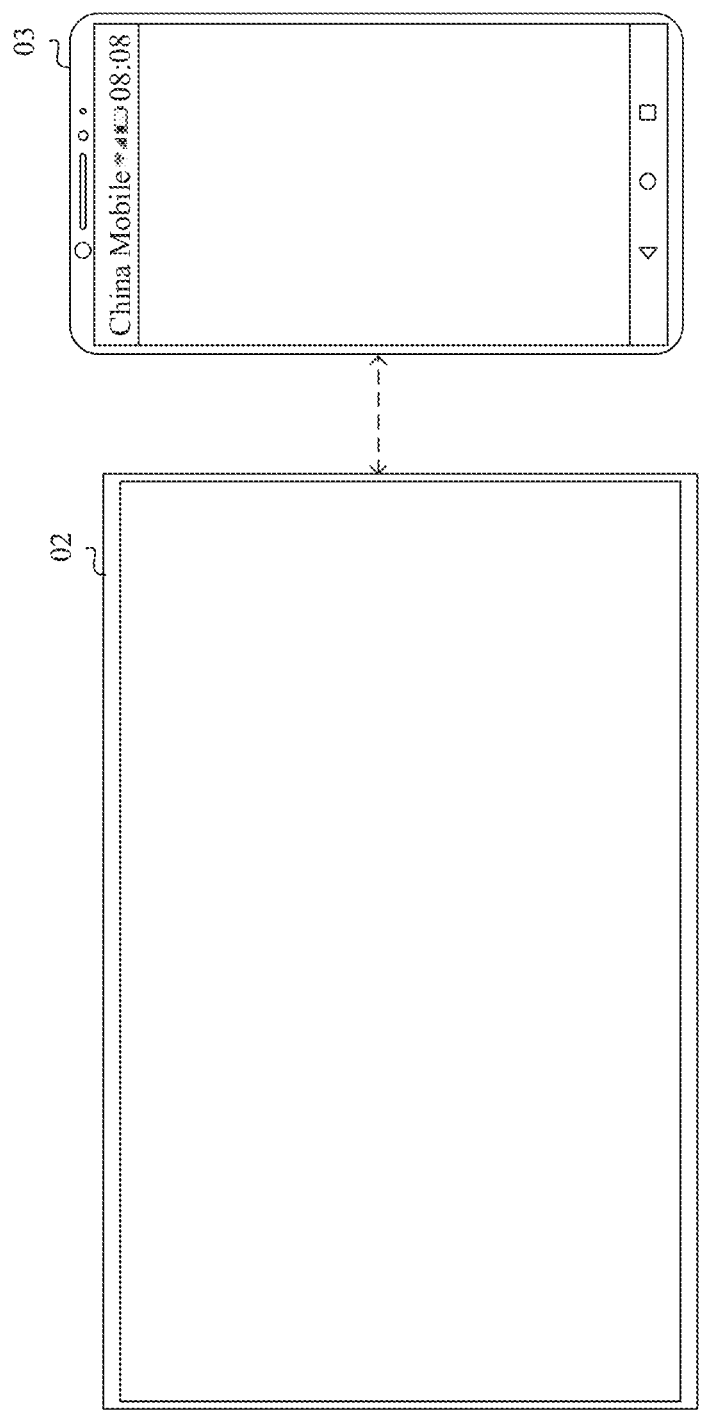
FIG. 1B is a schematic diagram of a system according to an embodiment of this application.

In some other embodiments, the intelligent voice playing method provided in the embodiments of this application may be further applied to a system shown in FIG. 1B. The system includes an electronic device 02 having a screen, and an electronic device 03 used in cooperation with the electronic device 02. The electronic device 02 or the electronic device 03 may include a camera, and the camera is configured to capture an image of real-time exercise of a user. The electronic device 02 or the electronic device 03 may include an audio player, and the audio player is configured to play a voice. For example, the electronic device 03 may be a mobile phone, a wearable device (for example, a watch or a wristband), a tablet computer, or a notebook computer.

For example, a large-screen television is used in cooperation with a mobile phone, and the screen of the television is configured to play a coach video and display an image of real-time exercise of a user. The mobile phone used in cooperation with the television may determine, in real time when the user performs exercise training according to the coach video, to-be-played voices for a current training state and training action of the user, and an audio player on the mobile phone or the television may perform voice playing.

Figure 2:
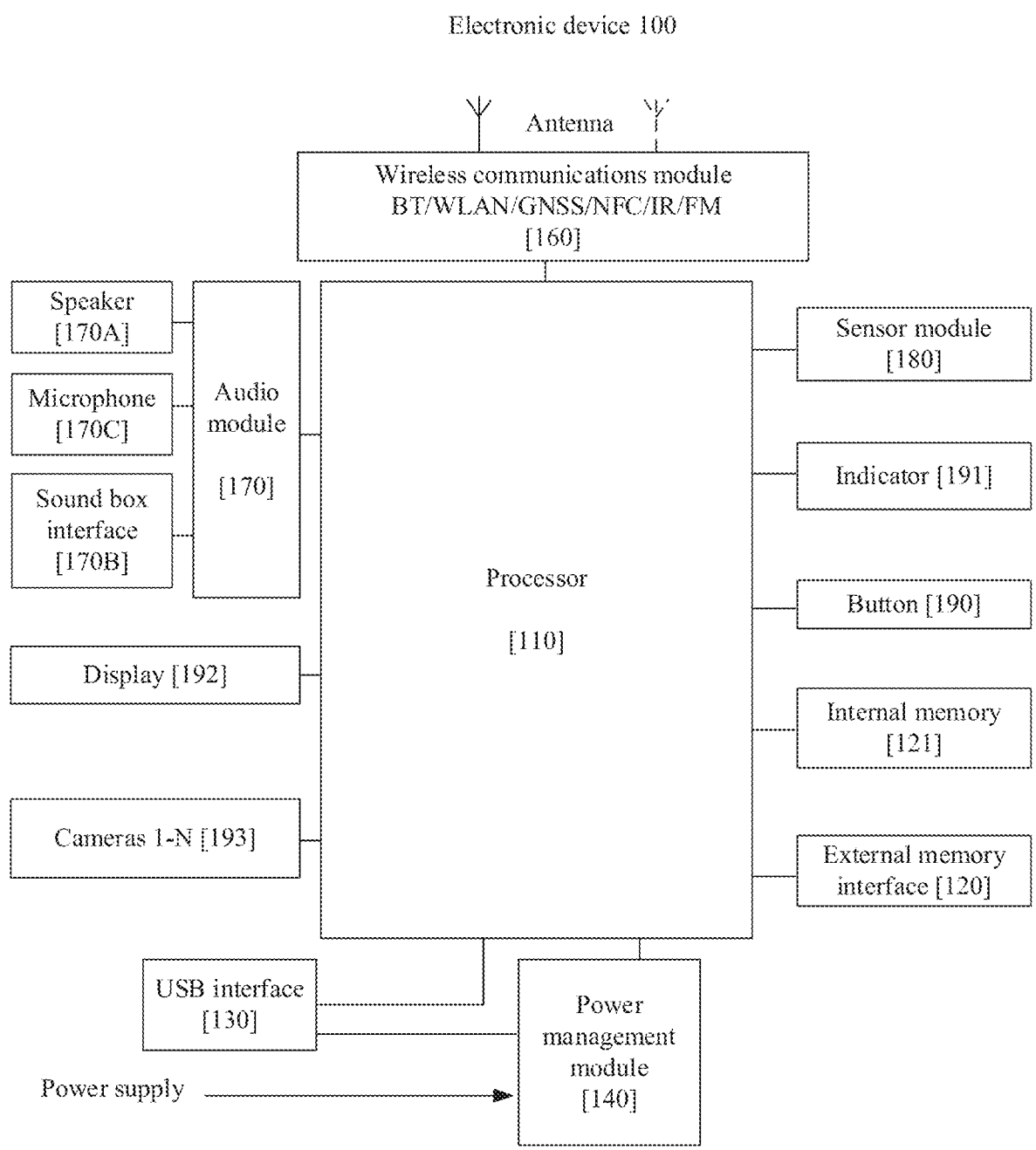
FIG. 2 is a schematic diagram of a structure of another electronic device according to an embodiment of this application.

For example, FIG. 2 is a schematic diagram of a structure of an electronic device 100 that uses the intelligent voice playing method provided in the embodiments of this application. As shown in FIG. 2, the electronic device 100 may include a processor 110, an external memory interface 120, an internal memory 121, a universal serial bus (universal serial bus, USB) interface 130, a power management module 140, an antenna, a wireless communications module 160, an audio module 170, a speaker 170A, a microphone 170C, a sound box interface 170B, a sensor module 180, a button 190, an indicator 191, a camera 193, a display 192, and the like.

The sensor module 180 may include a distance sensor, an optical proximity sensor, a fingerprint sensor, a temperature sensor, a touch sensor, an ambient light sensor, and the like.

It may be understood that a structure shown in the embodiments does not constitute a specific limitation on the electronic device 100. In some other embodiments, the electronic device 100 may include more or fewer components than those shown in the figure, or some components may be combined, or some components may be split, or different component arrangements may be used. The components shown in the figure may be implemented by using hardware, software, or a combination of software and hardware.

The processor 110 may include one or more processing units. For example, the processor 110 may include an application processor (application processor, AP), a modem processor, a graphics processing unit (graphics processing unit, GPU), an image signal processor (image signal processor, ISP), a controller, a memory, a video codec, a digital signal processor (digital signal processor, DSP), a baseband processor, and/or a neural-network processing unit (neural-network processing unit, NPU). Different processing units may be independent devices, or may be integrated into one or more processors.

The controller may be a nerve center and a command center of the electronic device 100. The controller may generate an operation control signal based on instruction operation code and a time sequence signal, to complete control of instruction fetching and instruction execution.

A memory may be further disposed in the processor 110, and is configured to store instructions and data. In some embodiments, the memory in the processor 110 is a cache. The memory may store instructions or data just used or cyclically used by the processor 110. If the processor 110 needs to use the instructions or the data again, the processor 110 may directly invoke the instructions or the data from the memory. This avoids repeated access and reduces waiting time of the processor 110, so that system efficiency is improved.

In some embodiments, the processor 110 may include one or more interfaces. The interface may include an inter-integrated circuit (inter-integrated circuit, I2C) interface, an inter-integrated circuit sound (inter-integrated circuit sound, I2S) interface, a pulse code modulation (pulse code modulation, PCM) interface, a universal asynchronous receiver/transmitter (universal asynchronous receiver/transmitter, UART) interface, a mobile industry processor interface (mobile industry processor interface, MIPI), a general-purpose input/output (general-purpose input/output, GPIO) interface, a USB interface, and/or the like.

It may be understood that an interface connection relationship between the modules shown in the embodiments is merely used as an example for description, and does not constitute a limitation on the structure of the electronic device 100. In some other embodiments, the electronic device 100 may alternatively use an interface connection manner different from that in the foregoing embodiment, or a combination of a plurality of interface connection manners.

The power management module 140 is configured to connect to a power supply. The charging management module 140 may be further connected to the processor 110, the internal memory 121, the display 194, the camera 193, the wireless communications module 160, and the like. The power management module 141 receives an input of the power supply and supplies power to the processor 110, the internal memory 121, the display 194, the camera 193, the wireless communications module 160, and the like. In some embodiments, the power management module 141 may alternatively be disposed in the processor 110.

A wireless communication function of the electronic device 100 may be implemented by using the antenna, the wireless communications module 160, or the like. The wireless communications module 160 may provide a wireless communication solution that includes a wireless local area network (wireless local area network, WLAN) (for example, a wireless fidelity (wireless fidelity, Wi-Fi) network), Bluetooth (Bluetooth, BT), a global navigation satellite system (global navigation satellite system, GNSS), frequency modulation (frequency modulation, FM), a near field communication (near field communication, NFC) technology, an infrared (infrared, IR) technology, or the like and that is applied to the electronic device.

The wireless communications module 160 may be one or more devices that integrate at least one communications processor module. The wireless communications module 160 receives an electromagnetic wave through the antenna 2, performs frequency modulation and filtering processing on the electromagnetic wave signal, and sends a processed signal to the processor 110. The wireless communications module 160 may further receive a to-be-sent signal from the processor 110, perform frequency modulation and amplification on the signal, and convert a processed signal into an electromagnetic wave through the antenna 2 for radiation. In some embodiments, the antenna of the electronic device 100 is coupled to the wireless communications module 160, so that the electronic device 100 may communicate with a network and another device by using a wireless communications technology.

The electronic device 100 implements a display function by using the GPU, the display 192, the application processor, and the like. The GPU is a microprocessor for image processing, and is connected to the display 192 and the application processor. The GPU is configured to: perform mathematical and geometric calculation, and render an image. The processor 110 may include one or more GPUs that execute program instructions to generate or change display information.

The display 192 is configured to display an image, a video, and the like. The display 192 includes a display panel. The display panel may be a liquid crystal display (liquid crystal display, LCD), an organic light-emitting diode (organic light-emitting diode, OLED), an active-matrix organic light-emitting diode (active-matrix organic light-emitting diode, AMOLED), a flexible light-emitting diode (flexible light-emitting diode, FLED), a mini-LED, a micro-LED, a micro-OLED, a quantum dot light-emitting diode (quantum dot light-emitting diode, QLED), or the like.

In this embodiment of this application, the display 192 may be configured to display a coach video and an image of real-time exercise of a user.

The electronic device 100 may implement a photographing function through the ISP, the camera 193, the video codec, the GPU, the display 192, the application processor, and the like. The ISP is configured to process data fed back by the camera 193. In some embodiments, the ISP may be disposed in the camera 193.

The camera 193 is configured to capture a static image or a video. An optical image of an object is generated through the lens, and is projected onto the photosensitive element. The light-sensitive element may be a charge coupled device (charge coupled device, CCD) or a complementary metal-oxide-semiconductor (complementary metal-oxide-semiconductor, CMOS) phototransistor. The photosensitive element converts an optical signal into an electrical signal, and then transmits the electrical signal to the ISP to convert the electrical signal into a digital image signal. The ISP outputs the digital image signal to the DSP for processing. The DSP converts the digital image signal into an image signal in a standard format such as an RGB format or a YUV format. In some embodiments, the electronic device 100 may include one or N cameras 193, where N is a positive integer greater than 1. For example, the camera 193 may be disposed at an upper edge of the display 192 of the electronic device 100. Certainly, a position of the camera 193 on the electronic device 100 is not limited in this embodiment of this application.

Alternatively, the electronic device 100 may not include a camera. In other words, the camera 193 is not disposed in the electronic device 100. The electronic device 100 may be externally connected to the camera 193 through an interface (for example, the USB interface 130). The external camera 193 may be fastened to the electronic device 100 by using an external fastener (for example, a camera support with a clip). For example, the external camera 193 may be fastened to an edge such as an upper side edge of the display 192 of the electronic device 100 by using the external fastener.

In this embodiment of this application, the camera 193 may be configured to capture the image of the real-time exercise of the user.

The digital signal processor is configured to process a digital signal, and may process another digital signal in addition to the digital image signal. For example, when the electronic device 100 selects a frequency, the digital signal processor is configured to perform Fourier transform on frequency energy and the like. The video codec is configured to; compress or decompress a digital video. The electronic device 100 may support one or more video codecs. In this way, the electronic device 100 can play or record videos in a plurality of coding formats, for example, moving picture experts group (moving picture experts group, MPEG)-1, MPEG-2, MPEG-3, and MPEG-4.

The NPU is a neural-network (neural-network, NN) computing processor. The NPU quickly processes input information with reference to a structure of a biological neural network, for example, a transfer mode between human brain neurons, and may further continuously perform self-learning. The NPU can implement applications such as intelligent cognition of the electronic device 100, such as image recognition, facial recognition, speech recognition, and text understanding.

The external memory interface 120 may be configured to connect to an external storage card, for example, a micro SD card, to extend a storage capability of the electronic device 100. The external storage card communicates with the processor 110 through the external memory interface 120, to implement a data storage function. For example, files such as music and a video are stored in the external storage card.

The internal memory 121 may be configured to store computer-executable program code. The executable program code includes instructions. The processor 110 runs the instructions stored in the internal memory 121, to perform various function applications of the electronic device 100 and data processing. For example, in this embodiment of this application, the processor 110 may execute the instructions stored in the internal memory 121, to perform the intelligent voice playing method provided in the embodiments of this application. The internal memory 121 may include a program storage area and a data storage area.

The program storage area may store an operating system, an application required by at least one function (for example, a sound playing function or an image playing function), and the like. The data storage area may store data (for example, audio data and an address book) and the like created when the electronic device 100 is used. In addition, the internal memory 121 may include a high-speed random access memory, or may include a nonvolatile memory, for example, at least one magnetic disk storage device, a flash memory, or a universal flash storage (universal flash storage, UFS).

In this embodiment of this application, the processor 110 may determine, in real time when the user performs exercise training according to the coach video, different voices for a current exercise state and exercise action of the user.

The electronic device 100 may implement an audio function such as music playing or recording by using the audio module 170, the speaker 170A, the microphone 170C, the sound box interface 170B, the application processor, and the like.

The audio module 170 is configured to convert digital audio information into an analog audio signal output, and is also configured to convert an analog audio input into a digital audio signal. The audio module 170 may be further configured to: code and decode an audio signal. In some embodiments, the audio module 170 may be disposed in the processor 110, or some functional modules of the audio module 170 are disposed in the processor 110. The speaker 170A, also referred to as a "loudspeaker", is configured to convert an audio electrical signal into a sound signal. The microphone 170C, also referred to as a "mike" or a "mic", is configured to convert a sound signal into an electrical signal.

The sound box interface 170B is configured to connect to a wired sound box. The sound box interface 170B may be the USB interface 130, or may be a 3.5 mm open mobile terminal platform (open mobile terminal platform, OMTP) standard interface, or a cellular telecommunications industry association of the USA (cellular telecommunications industry association of the USA, CTIA) standard interface.

In this embodiment of this application, the speaker 170A, or the sound box interface 170B and a connected sound box, may be configured to play the different voices determined by the processor 110 for the current exercise state and exercise action of the user in real time when the user performs exercise training according to the coach video.

The button 190 includes a power button, a volume button, and the like. The button 190 may be a mechanical button, or may be a touch button. The electronic device 100 may receive a key input, and generate a key signal input related to a user setting and function control of the electronic device 100.

The indicator 191 may be an indicator light, and may be configured to indicate that the electronic device 100 is in a power-on mode, a standby mode, a power-off mode, or the like. For example, the indicator light being off may indicate that the electronic device 100 is in the power-off mode. The indicator light being green or blue may indicate that the electronic device 100 is in the standby mode. The indicator light being red may indicate that the electronic device 100 is in the standby mode.

The electronic device 100 is usually equipped with a remote control. The remote control is configured to control the electronic device 100. The remote control may include a plurality of buttons, such as a power button, a volume button, and a plurality of other selection buttons. The button on the remote control may be a mechanical button, or may be a touch button. The remote control may receive a key input, generate a key signal input related to a user setting and function control of the electronic device 100, and send a corresponding control signal to the electronic device 100, to control the electronic device 100. For example, the remote control may send a control signal to the electronic device 100 through an infrared signal or the like. The remote control may further include a battery storage cavity that is configured to mount a battery and supply power to the remote control.

It may be understood that the structure shown in this embodiment of this application does not constitute a specific limitation on the electronic device 100. The electronic device 100 may have more or fewer components than those shown in FIG. 2, or may combine two or more components, or may have different component configurations. For example, the electronic device may further include a component such as a sound box. Various components shown in FIG. 2 may be implemented in hardware, software, or a combination of hardware and software that includes one or more signal processing or application-specific integrated circuits.

It may be understood that the electronic device 100 may alternatively include components different from the above, which may have more or fewer components than those shown in FIG. 2, may combine two or more components, or may have different component configurations. This is not limited in this embodiment of this application.

In this embodiment of this application, the camera 193 in the electronic device 100 shown in FIG. 2 may be configured to capture the image of the real-time exercise of the user. The display 192 may be configured to display the coach video and the image of the real-time exercise of the user. The processor 110 may determine, in real time and based on a preset rule when the user performs exercise training according to the coach video, different voices for a current exercise state and exercise action of the user. The speaker 170A may be configured to play a voice determined by the processor 110. In this way, when the user performs exercise training according to the coach video, the electronic device may play different voices in real time for a current exercise state and exercise action of the user, to provide the user with real-time voice feedback and guidance for action improvement. In addition, voice content is abundant and diversified, and user experience is relatively good.

The intelligent voice playing method in the embodiments of this application is described below by using an electronic device having the structure shown in FIG. 2 as an example.

In the intelligent voice playing method provided in the embodiments of this application, voices that can be played by the electronic device includes a main flow voice and a non-main flow voice. The main flow voice may include one or more of types such as an action improvement voice, a training tempo voice, an action evaluation voice, and the like. When a user performs exercise training according to a coach video, the electronic device may play, in real time, a plurality of different types of voices for a current exercise state and exercise action of the user, so that played voice content is abundant and diversified, and voice content is not easily repeated, which can avoid a monotonous feeling caused by playing a fixed set of voices, increase training interest of the user, and improve usage experience of the user.

In addition, each type of voice may further include voice prompts of a plurality of dimensions. In this way, the electronic device may provide voice prompts to the user from different dimensions and angles, so that voice content of voices that can be played may be more abundant, the voice content may be flexible and diversified, and voice prompts are more specific and comprehensive, which can give the user a fresh and interesting feeling, and improve usage experience of the user.

The main flow voice may be used to introduce some related information of a current training course to the user, to ensure that a training flow is normally performed, and the like. For example, the main flow voice may include one or more of a plurality of dimensions such as a flow-based voice, a position adjustment voice, a stance adjustment voice, or a humanized prompt voice.

The flow-based voice is used to introduce related information of a current course progress, for example, may include a voice used to introduce an action name and a set quantity, an action start prompt voice, and an action end prompt voice. For example, the flow-based voice may be "Welcome to the fitness system, first section, hand-assisted squatting, three sets in total, and each with five actions". For another example, the action end prompt voice may be "Nice, you have finished the first section of training actions" or "Wow, amazing, it seems that you have mastered the key action point, keep going for the next".

The position adjustment voice may be used to prompt the user to stand at a specific position, so that the camera can capture an image of the user, to ensure that training can be performed normally. For example, the position adjustment voice for the user may be "Please stand in front of the screen" or "Please move to the middle area of the screen".

The stance adjustment voice may be used to prompt the user to adjust a stance orientation, so that the camera can capture an image of a specific part of the user, to ensure that training can be performed normally. For example, the position adjustment voice for the user may be "Please stand sideways to the screen".

The humanized prompt voice may be used to give the user some humanized prompts. For example, when determining, by using the image captured by the camera, that the user is relatively close to a table corner, the electronic device may prompt the user by using a voice "Please keep away from the table corner to avoid getting hurt".

The electronic device may determine, based on a progress of a training course, whether to play the flow-based voice. The electronic device may determine, based on a state such as a position and an orientation of the user, whether to play the position adjustment voice or the stance adjustment voice. The electronic device may determine, based on a state such as an environment in which the user is currently located, whether to play the humanized prompt voice.

For example, for examples of content of the main flow voice, refer to Table 1.

TABLE 1

| | Main flow voice |
|---|---|
| Flow-based voice | Training is about to start, please get ready. Three, two, one, go. You have finished all the actions. You have finished the first section of actions. Wow, amazing, it seems that you have mastered the key action point, keep going for the next . . . |
| Position adjustment voice | Please stand in front of the screen. Please move to the left. Please move to the right . . . |
| Stance adjustment voice | Please turn your head right. Please stand on your side. Please stand facing the screen . . . |
| Humanized prompt voice | Please keep away from the table corner. Please keep away from the wall... |

The action improvement voice is used to guide the user to improve a training action, and improve a standard degree of the training action. The action evaluation voice is used to affirm, encourage, and praise a training action of the user. When the user performs exercise training, the electronic device may determine, based on a captured image of the user and a preset detection algorithm, a degree of matching between a training action of the user and a standard action in the coach video.

If the degree of matching between the training action of the user and the standard action in the coach video is relatively small, the electronic device may guide, by using the action improvement voice, the user to improve the standard degree of the action, so that the user can learn a deficiency and an improvement direction in time from real-time voice feedback, to adjust and improve action quality in time.

In the embodiments of this application, the action improvement voice is a positive guiding voice, which is used to help the user improve the action quality with an error corrected, instead of continuously and simply indicating that a training action of the user is erroneous or non-standard, leading to relatively poor user experience. Moreover, even if it is indicated that the training action of the user is erroneous or an action of a part is not standard, the user usually does not know how to improve the action.

In the embodiments of this application, the electronic device may play, in real time for a current exercise action of the user, an action improvement voice for improving quality of the current training action, to guide the user in real time for the current training action, and instruct the user to perform a more standard action. Moreover, the action improvement voice may be brief and easy-to-understand language content inclined to be colloquial.

For example, the action improvement voice may include one or more of a plurality of dimensions such as a frequency improvement voice, a range improvement voice, or a posture improvement voice. For example, for examples of content of the action improvement voice, refer to Table 2.

TABLE 2

Action improvement voice

| | |
|---|---|
| Frequency | Moving a little faster would be better, come on. Move a little slower, keep the tempo. Move a little faster. Move a little slower . . . |
| Range | Great, get the action range a little bigger. The action range is too small to achieve the exercise effect. Get your arms a little bigger swinging range. Come on, jump a little higher . . . |
| Posture | Raise the knee a little higher when lifting the knee. Keep the knee and toes in the same direction. Get the spine straight and keep the trunk upright during squatting. Stretch your arms as straight as possible and clap the hands on top of your head . . . |

If the degree of matching between the training action of the user and the standard action in the coach video is relatively large, the electronic device may give the user positive encouragement by using the action evaluation voice, to increase confidence and a sense of achievement of the user, and improve a sense of interest of the user.

For example, the action evaluation voice may include a plurality of dimensions such as a perfect level and an awesome level. For example, for examples of content of the action evaluation voice, refer to Table 3.

TABLE 3

Action evaluation voice

| | |
|---|---|
| Perfect level | Perfect action. It is exactly like the coach did. That is so standard, keep going. Good job . . . |
| Awesome level | You can do a little better. Awesome, try harder. Pay attention to the action details, it is just a little different. Well done . . . |

In an exercise training process, if an action frequency is relatively fast or a quantity of required actions is relatively large, it is not easy for the user to remember a quantity of actions. The user is not clear how many actions have been performed and how many actions remain to be performed, or the user does not want to remember how many actions have been performed. The electronic device may prompt, by using the training tempo voice, a progress of a current training action, to help the user learn how many sets/actions remain to be performed, and how many sets/actions have been performed, and help the user understand a progress status of the course, thereby adjusting physical and mental states. Alternatively, the user may be a little tired in the exercise process, and the electronic device may prompt, by using the training tempo voice, the user how many sets are left and it will be over soon, to help the user hold on.

For example, for examples of content of the training tempo voice, refer to Table 4.

TABLE 4

Training tempo voice
The last set, come on
You have mastered it, just two sets left
Great, only three sets left TABLE 4-continued Five more actions, come on
Hold on, just the last action left
. . .

By using the voice prompts of the plurality of types and the plurality of dimensions, the electronic device may guide, correct, and encourage the user in real time by using voices in the exercise training process of the user, to instruct the user to smoothly perform exercise training.

Figure 3:
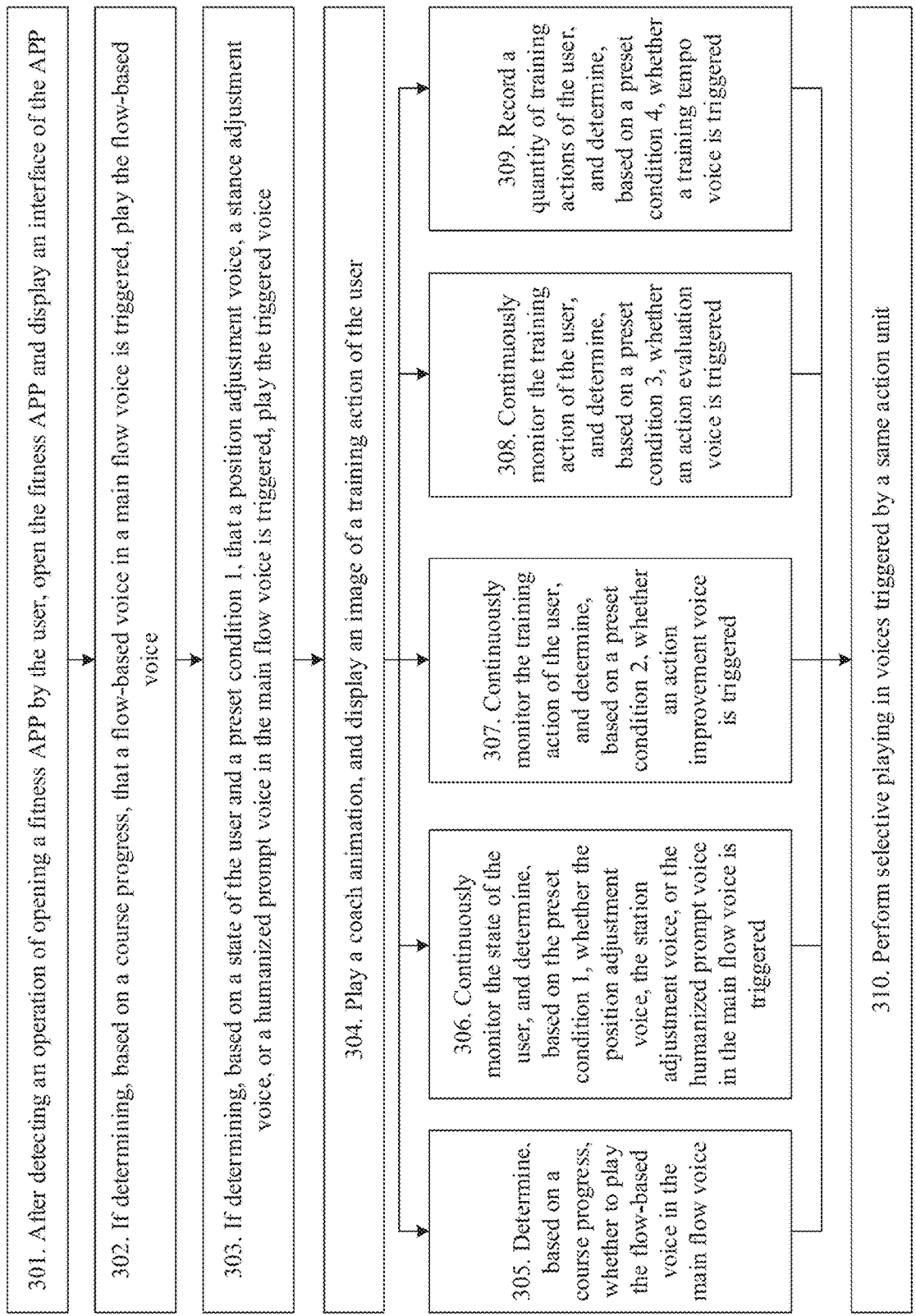
FIG. 3 is a flowchart of voice playing according to an embodiment of this application.

The intelligent voice playing method provided in the embodiments of this application is described below by using an example in which a user performs fitness training. Refer to FIG. 3. The method may include the following steps.

301. After detecting an operation of opening an AI fitness APP by the user, the electronic device opens the AI fitness APP and displays an interface of the APP.

The electronic device may detect an operation of instructing, by the user by using a remote control, a voice instruction, or the like, the electronic device to open the AI fitness APP. Alternatively, if a screen of the electronic device is a touchscreen, the electronic device may further detect a touch operation of instructing, by the user, to open the AI fitness APP. After detecting the operation of opening the AI fitness APP by the user, the electronic device may open the AI fitness APP, to start a fitness course.

Figure 4A:
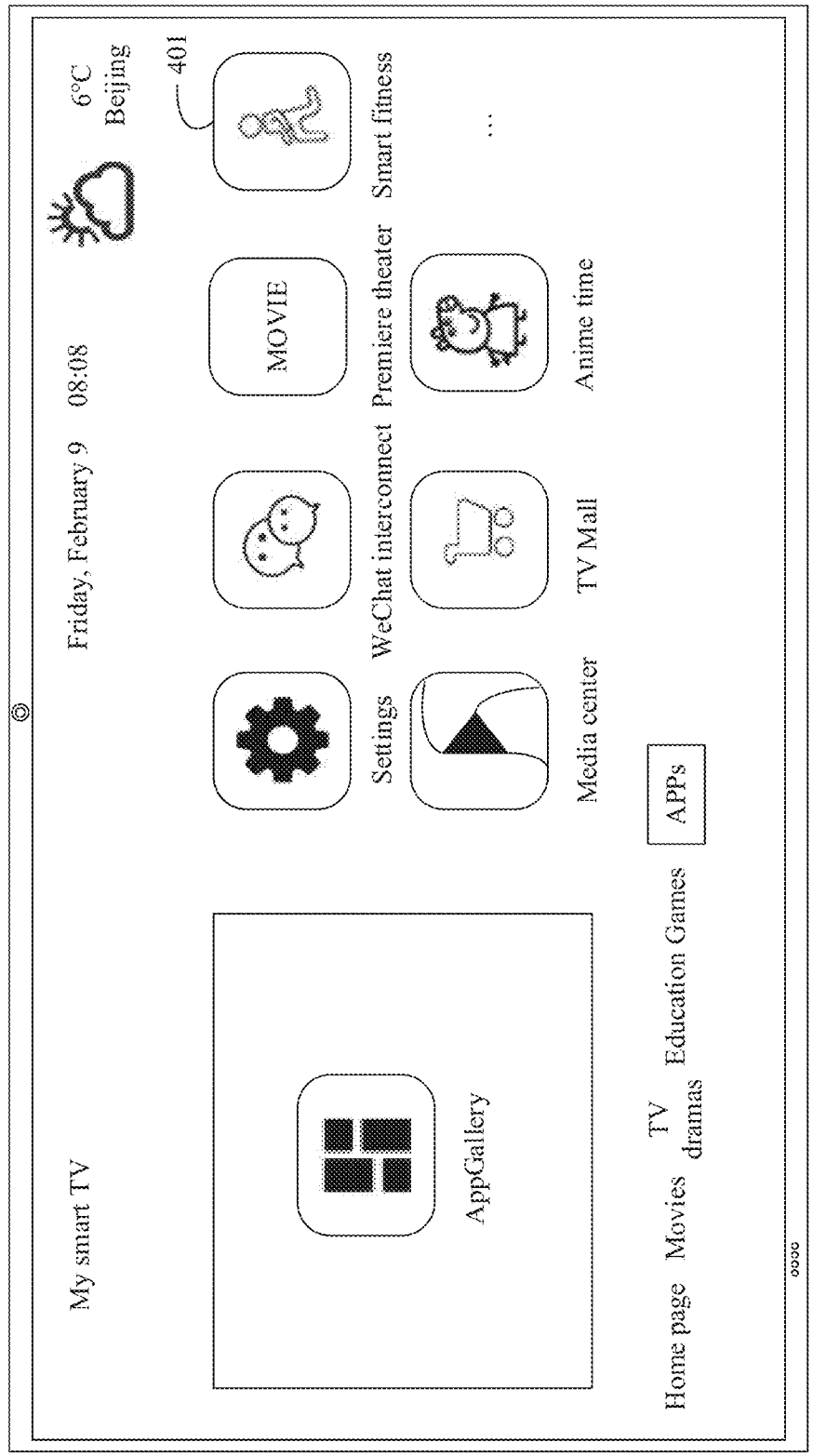
FIG. 4(a) to FIG. 4(c) are schematic diagrams of a set of interfaces according to an embodiment of this application.
Figure 4B:
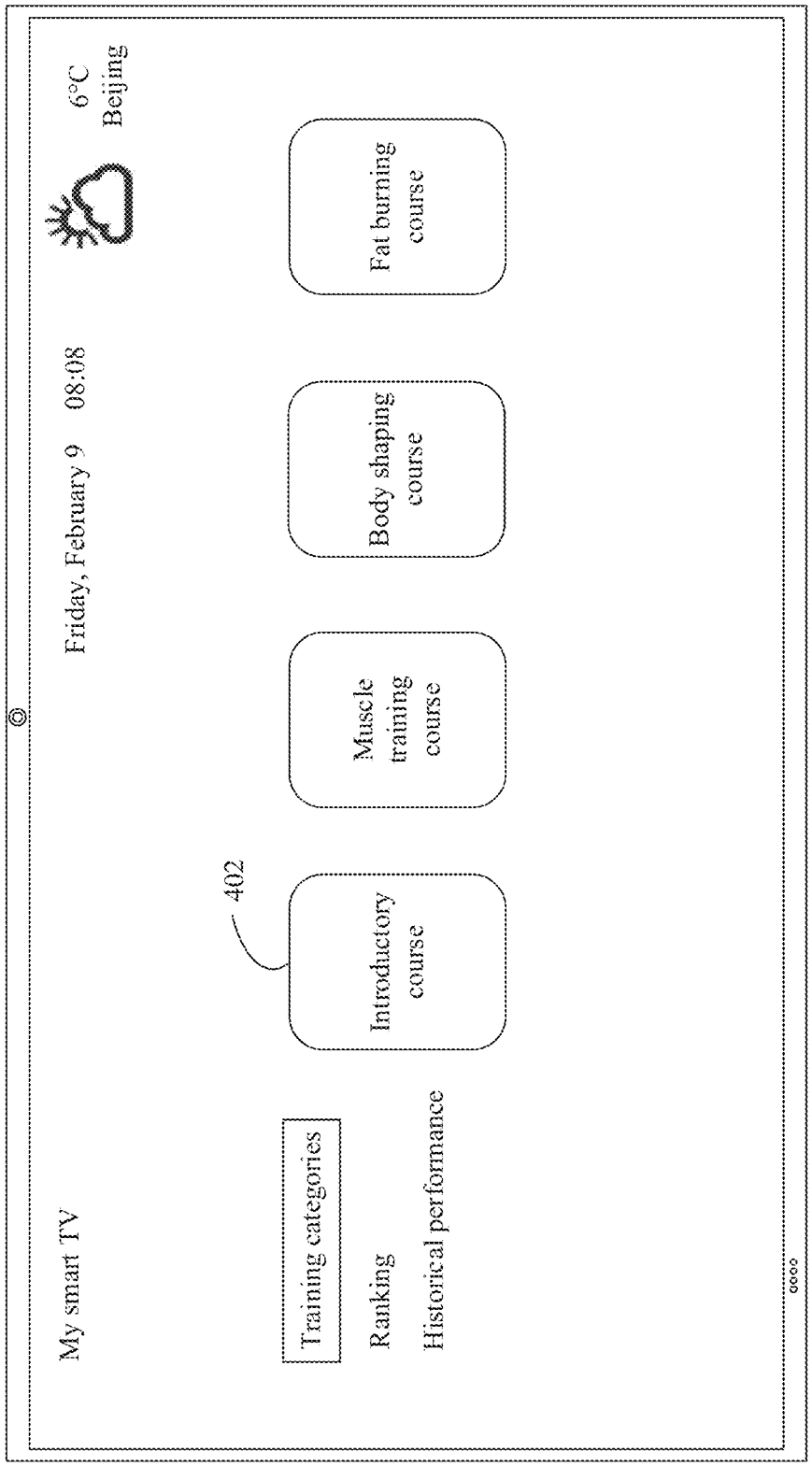

For example, referring to FIG. 4(a), the electronic device displays an AI fitness APP icon 401. After detecting an operation of clicking the AI fitness APP icon 401 by the user by using a remote control, the electronic device opens the AI fitness APP, and displays an interface, shown in FIG. 4(b), of the AI fitness APP. Then, after detecting an operation of selecting a fitness course (for example, an introductory course 402) by the user, the electronic device starts the fitness course, and displays an interface shown in FIG. 4(c).

302. If the electronic device determines, based on a course progress, that a flow-based voice in a main flow voice is triggered, the electronic device plays the flow-based voice.

After the course starts, the electronic device may play the flow-based voice based on the course progress, to introduce related information of the current training course to the user, explain and describe a training action to be performed by the user, and the like. For example, the electronic device may play the flow-based voice when the course starts. For example, the flow-based voice may be "Welcome to the fitness introductory course" or "Training is about to start, please get ready!".

In some embodiments, the electronic device may further display text information of the flow-based voice on the screen, to further prompt the user visually.

303. If the electronic device determines, based on a state of the user and a preset condition 1, that a position adjustment voice, a stance adjustment voice, or a humanized prompt voice in the main flow voice is triggered, the electronic device plays the triggered voice.

The state of the user includes a position, a stance orientation, an environment in which the user is located, and the like of the user. For example, when the preset condition 1 is that the user is not within a capture field of view range of the camera, the electronic device determines that the position adjustment voice is triggered. For another example, when the preset condition 1 is that a stance orientation of the user does not meet a preset angle, the electronic device determines that the stance adjustment voice is triggered. For another example, when the preset condition 1 is that the user is relatively close to a dangerous object, the electronic device determines that the humanized prompt voice is triggered.

The electronic device may determine, based on the state of the user and the preset condition 1, whether the position adjustment voice, the stance adjustment voice, or the humanized prompt voice in the main flow voice is triggered, to prompt the user to adjust the state such as the position or the orientation of the user in time, so as to ensure that the user can normally start fitness training.

Figure 4C:
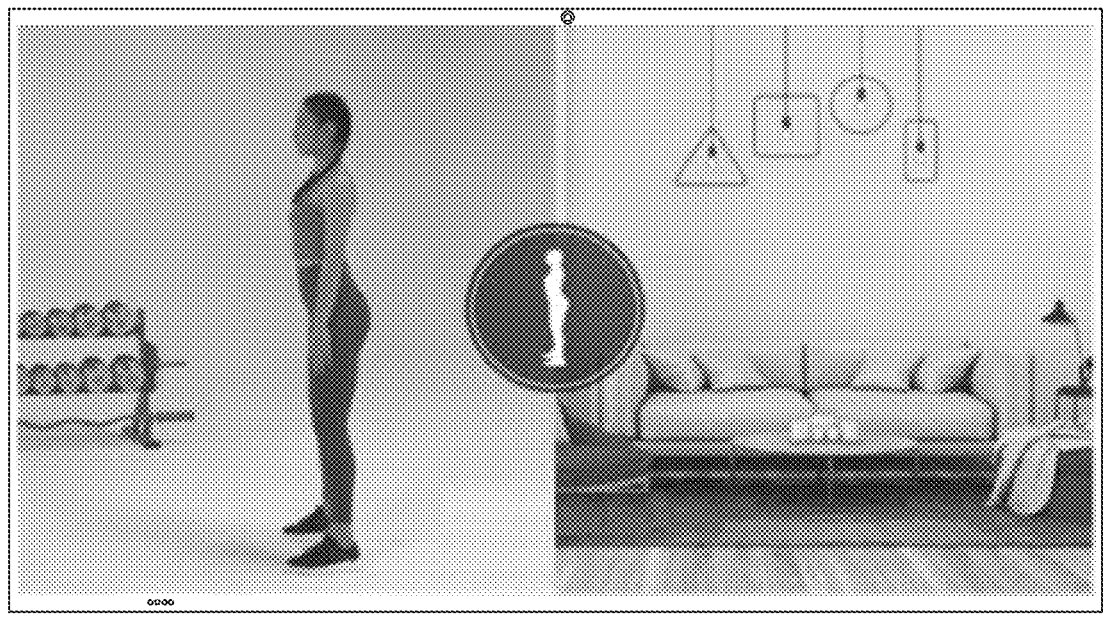

For example, in a case shown in FIG. 4(c), if the camera of the electronic device has not detected the user, the electronic device determines that a main flow voice "Please stand in front of the screen" is triggered.

In some embodiments, when playing the main flow voice such as the position adjustment voice, the stance adjustment voice, or the humanized prompt voice, the electronic device may display first graphic and text information on the screen. The first graphic and text information is graphic and text information corresponding to the main flow voice.

For example, the electronic device may display the first graphic and text information in a form of a task card on a side where an image of the user is displayed, to help the user learn, according to the first graphic and text information, a target that needs to be adjusted and improved in the state of the user. The first graphic and text information may be a more concise graphic and text representation for the main flow voice. For example, for the first graphic and text information in the form of the task card, refer to prompt information 501 in FIG. 5A.

In addition, the electronic device may further display first graphic and text information in the middle of the screen, to help the user see related prompt content more easily. For example, the first graphic and text information may further include prompt information 502 in FIG. 5A.

Figure 5A:
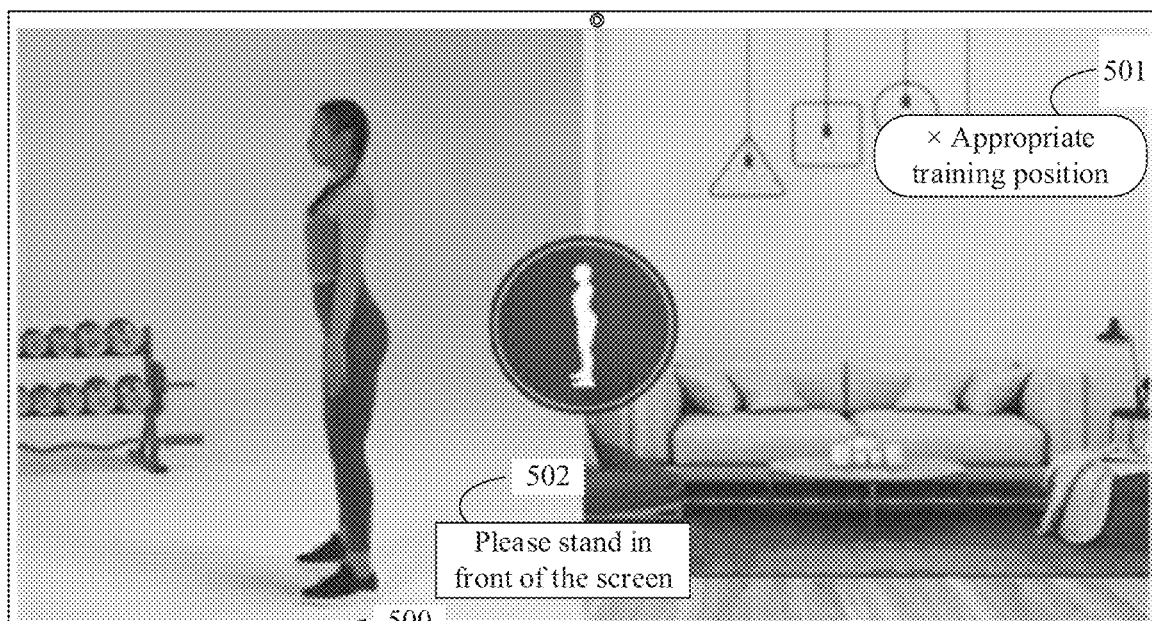
FIG. 5A is a schematic diagram of a voice prompt and interface display effect according to an embodiment of this application.

It should be noted that information 500 shown in FIG. 5A represents the main flow voice played by the electronic device.

Figure 5B:
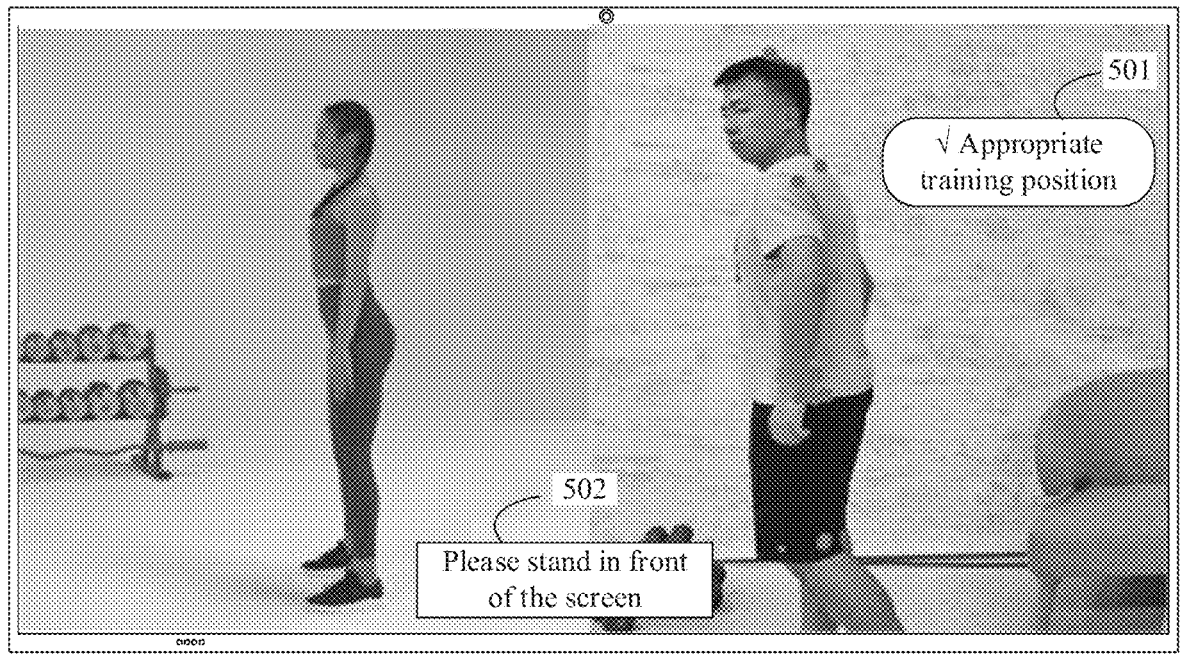
FIG. 5B is a schematic diagram of an interface display effect according to an embodiment of this application.
Figure 5C:
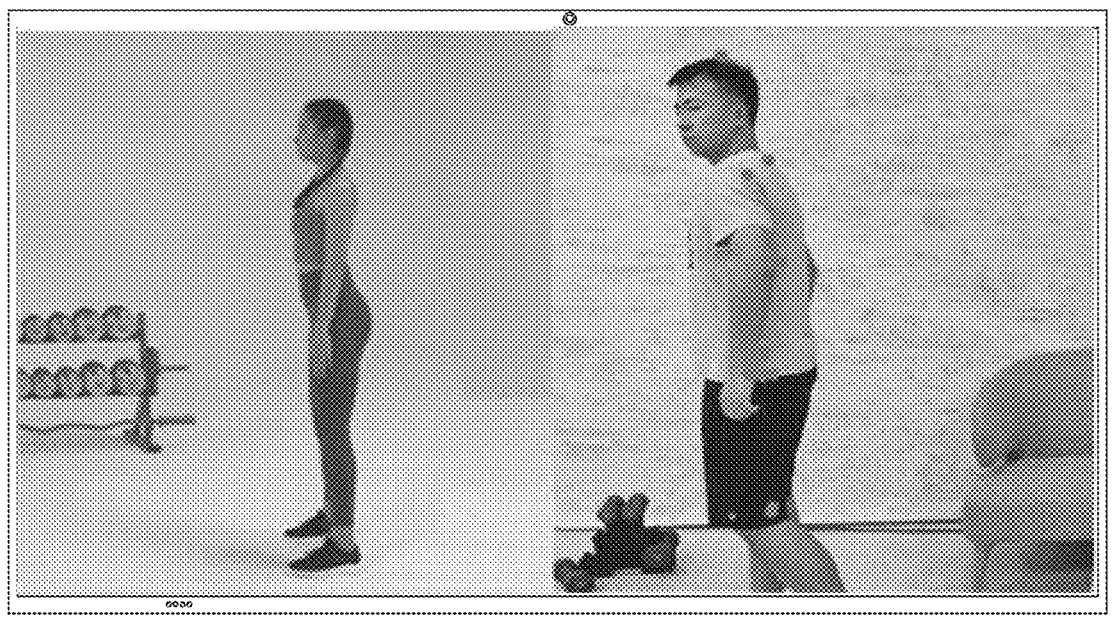
FIG. 5C is a schematic diagram of another interface display effect according to an embodiment of this application.

After the electronic device determines that the user adjusts, according to the main flow voice and the first graphic and text information, the state of the user to a state required by the first graphic and text information, the first graphic and text information in the form of the task card on the electronic device may be correspondingly changed, to respond to the state adjustment of the user. For example, a completion identifier may be displayed on the first graphic and text information. For example, referring to FIG. 5B, after detecting that the user stands in front of the screen, the electronic device may update a cross before the prompt information 501 to a check. The check may be the completion identifier. In some embodiments, as the first graphic and text information in the form of the task card changes, the electronic device may further play a response voice (for example, a beep). Then, referring to FIG. 5C, the first graphic and text information on the screen disappears. The electronic device resumes playing a coach video to continue a subsequent course.

If the electronic device detects that the user has not adjusted the state to the state required by the first graphic and text information, the first graphic and text information is continuously displayed. The first graphic and text information does not disappear, the course does not proceed, and subsequent content of the coach video is not played.

If the electronic device determines, based on a same state of the user, that a plurality of main flow voices are triggered, the electronic device may play each main flow voice separately. For example, the plurality of main flow voices may include "Please stand in front of the screen", "Please turn sideways to the screen", and "Please get your head back to the screen". After determining that the user adjusts, according to the plurality of main flow voices and corresponding first graphic and text information, the state of the user to a state required by the first graphic and text information, the electronic device stops displaying the first graphic and text information, and continue a subsequent course.

304. The electronic device plays the coach video, and displays an image of a training action of the user.

After the course starts, the electronic device may play the coach video. The coach video is an video of a standard action of a coach, and the user may perform the training action with reference to the coach video. The electronic device may further capture the image of the training action (or referred to as a fitness action or an exercise action) of the user, and display the image on the screen of the electronic device. That is, the electronic device may display both an image of the coach video and the image of the training action of the user on the screen, to help the user learn a degree of matching between the training action of the user and the standard action in the coach video through comparison. For example, for an interface displayed on the electronic device in the fitness training process of the user, refer to FIG. 6.

In some embodiments, the electronic device may further display preset bone nodes on the image of the training action of the user, so that the user more accurately determines a key part and a difference from the standard action of the coach based on the bone nodes, and adjusts and improves the action. For example, the bone nodes may be shown as dots 601 in FIG. 6.

Then, when the user performs fitness training according to the course, the electronic device may determine whether a main flow voice, an action improvement voice, an action evaluation voice, and a training tempo voice are triggered.

After step 304, the method may further include the following steps.

305. The electronic device determines, based on a subsequent course progress, whether to play the flow-based voice in the main flow voice.

For example, during the course, the electronic device may play the flow-based voice when each set of actions starts, to provide a related description and prompt for a training action to be performed. For example, when a set of actions starts, the flow-based voice may prompt a name of the set of actions and a quantity of sets, for example, "Next set of actions . . . " or "Three, two, one, go!".

For another example, after each set of actions ends or after the course ends, the electronic device may play the flow-based voice. For example, the flow-based voice may be "You have finished all the actions!".

306. The electronic device continuously monitors the state of the user, and determines, based on the preset condition 1, whether the position adjustment voice, the stance adjustment voice, or the humanized prompt voice in the main flow voice is triggered.

The electronic device may continuously monitor the state of the user, and determine, based on the preset condition 1, whether the position adjustment voice, the station adjustment voice, or the humanized prompt voice in the main flow voice is triggered, to prompt the user to adjust the state such as the position and the orientation of the user in time, so as to ensure that the user can normally perform fitness training.

307. The electronic device continuously monitors the training action of the user, and determines, based on a preset condition 2, whether an action improvement voice is triggered.

For example, the preset condition 2 may include a relatively small degree of matching between the training action of the user and the standard action in the coach video. The action improvement voice may be used to guide the user in real time for the current training action, and instruct the user to perform a more standard action.

308. The electronic device continuously monitors the training action of the user, and determines, based on a preset condition 3, whether an action evaluation voice is triggered.

For example, the preset condition 3 may include a relatively large degree of matching between the training action of the user and the standard action in the coach video. The action evaluation voice may be used to positively encourage the user for the current training action, to increase confidence and a sense of achievement of the user, and improve a sense of interest of the user.

309. The electronic device records a quantity of training actions of the user, and determines, based on a preset condition 4, whether a training tempo voice is triggered.

For example, the preset condition 4 is that the user is halfway in a set of actions. The training tempo voice is used to prompt that the user is halfway. For another example, the preset condition 4 is that a set of actions have N actions left, and a value of N is relatively small, for example, may be 1, 2, or 5. The training tempo voice is used to prompt the user that the set of actions will be over soon, and prompt the user to hold on.

310. The electronic device performs selective playing in voices triggered by a same action unit.

Because there are relatively large quantities of voice types and dimensions, the electronic device usually determines, based on the state and the action of the user by performing step 305 to step 309, that a plurality of to-be-played voices are triggered. To ensure timeliness of voice playing, avoid that the user already performs a next action but the electronic device still plays a related voice of the current action, avoid playing conflict between a plurality of voices so that the played voice can correspond to the training action of the user, and ensure that voice playing matches the training action of the user in real time, the electronic device may select a voice from the plurality of to-be-played voices for playing. In other words, the electronic device may perform selective playing in voices triggered by a same action unit.

The action unit is a unit preset by the electronic device for performing selective voice playing. That the electronic device performs selective playing in voices triggered by a same action unit means that the electronic device performs selective playing in a non-main flow voice triggered by an action in the same action unit and a main flow voice triggered by a state of the user in a process of performing an action in the same action unit.

The action unit may be one training action, or the action unit may be a part of one training action. For example, for a training action of dumbbell lateral flexion, one training action of dumbbell lateral flexion may include a first action unit and a second action unit. The first action unit includes holding a dumbbell with one hand and placing the other hand behind the head. The second action unit includes flexing the body to a side where the dumbbell is held. In one training action of dumbbell lateral flexion, if the first action unit triggers two voices, the electronic device performs selective playing in the two voices. If the second action unit triggers three voices, the electronic device performs selective playing in the three voices.

In another example, for a training action of squatting, one training action of squatting is an action unit. If one training action of squatting triggers four voices, the electronic device performs selective playing in the four voices.

It may be understood that, the electronic device may perform selective playing when a current action unit is performed, and does not necessarily perform selective playing after the current action unit is performed. For example, for the training action of squatting, the user is generally required to follow a key action point in a squatting process, and there is basically no special key point requirement when the user stands up after squatting. Therefore, after the squatting ends, the electronic device may perform selective playing in voices triggered in the squatting process of the user. When the user stands up after squatting, the playing of the voice may have been completed, and does not conflict with that of a next training action.

If playing of a voice selected to be played by the electronic device for an action unit is indeed not completed in a process of performing the action unit, the course and the training action of the user may proceed, and the voice is not interrupted, but continued until the playing is completed. A voice triggered by a subsequent action unit in the voice playing process is discarded. For example, one training action of squatting is an action unit, and the user performs three squats. For the first squat of the user, the electronic device selects a voice 1 from a plurality of triggered voices, and plays the voice 1. If the playing of the voice 1 is not completed after the first squat is completed, the voice 1 is continued in a process of performing the second squat. In addition, the electronic device discards a voice triggered by the second squat. If the playing of the voice 1 is completed in the third squat, the electronic device performs selective playing in a plurality of voices triggered by the third squat.

In this embodiment of this application, a plurality of voices of a plurality of types and a plurality of dimensions may be triggered by the electronic device for a same action unit, and the electronic device performs selective voice playing in these voices, so that voice playing content is not easily repeated, but unpredictable and flexible. In addition, a played voice corresponds to a training action and state of the user in real time.

In some embodiments, for voices triggered by a same action unit, the electronic device may select the first triggered voice based on a triggering sequence for playing.

In some other embodiments, the electronic device may perform, based on priorities of voices, selective playing in a plurality of voices triggered by a same action unit. A high-priority voice is more important than a low-priority voice. That is, the electronic device may preferentially play an important voice.

For example, in a priority assignment manner 1, the main flow voice has a higher priority non-main flow voices such as the action improvement voice, the training tempo voice, and the action evaluation voice. For another example, in a priority assignment manner 2, the main flow voice has a higher priority than the action improvement voice, and the action improvement voice has a higher priority than the action evaluation voice and the training tempo voice.

In one case, if the electronic device determines, based on a state of the user in a process of performing a same action unit by the user, that a plurality of main flow voices are triggered, because functions of the main flow voices are relatively important and priorities of the main flow voices are relatively high, the electronic device may play each main flow voice separately, to ensure that fitness training of the user can be normally performed. Specifically, the electronic device may sequentially play each main flow voice based on a triggering sequence.

Figure 7A:
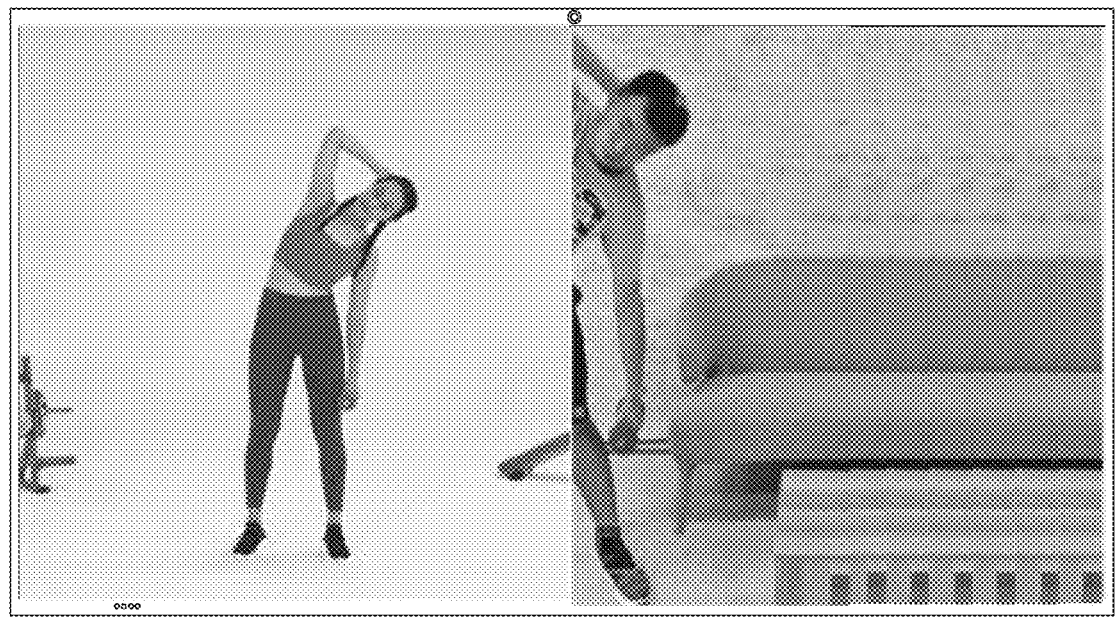
FIG. 7A is a schematic diagram of another interface display effect according to an embodiment of this application.
Figure 7B:
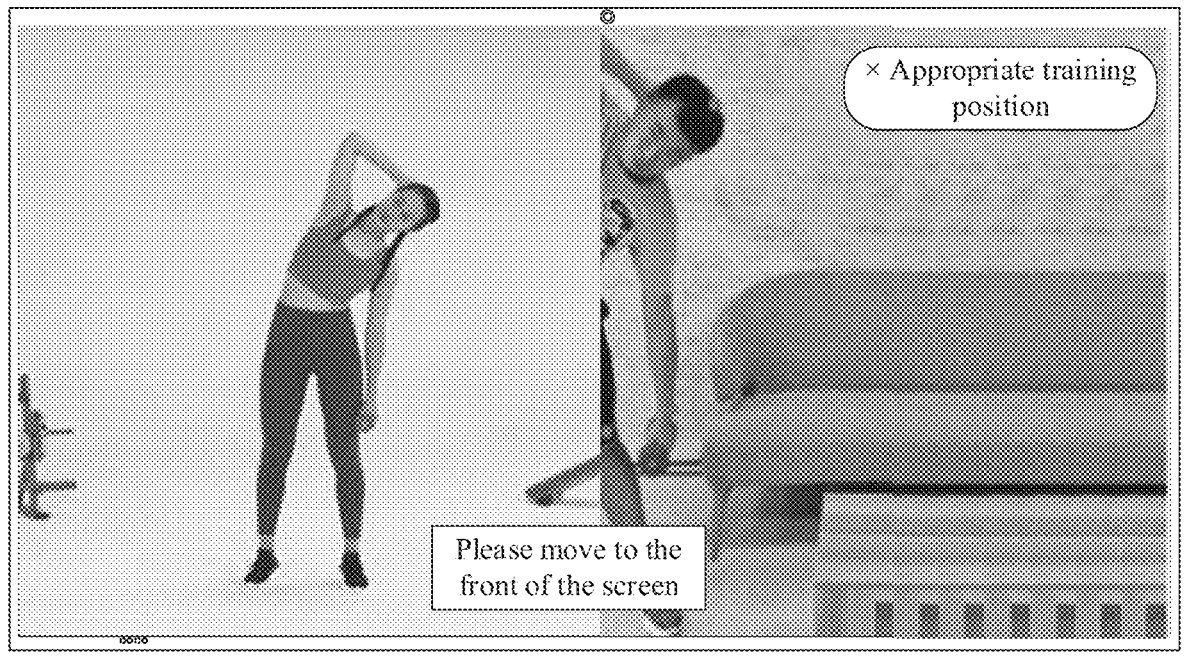
FIG. 7B is a schematic diagram of another voice prompt and interface display effect according to an embodiment of this application.
Figure 7C:
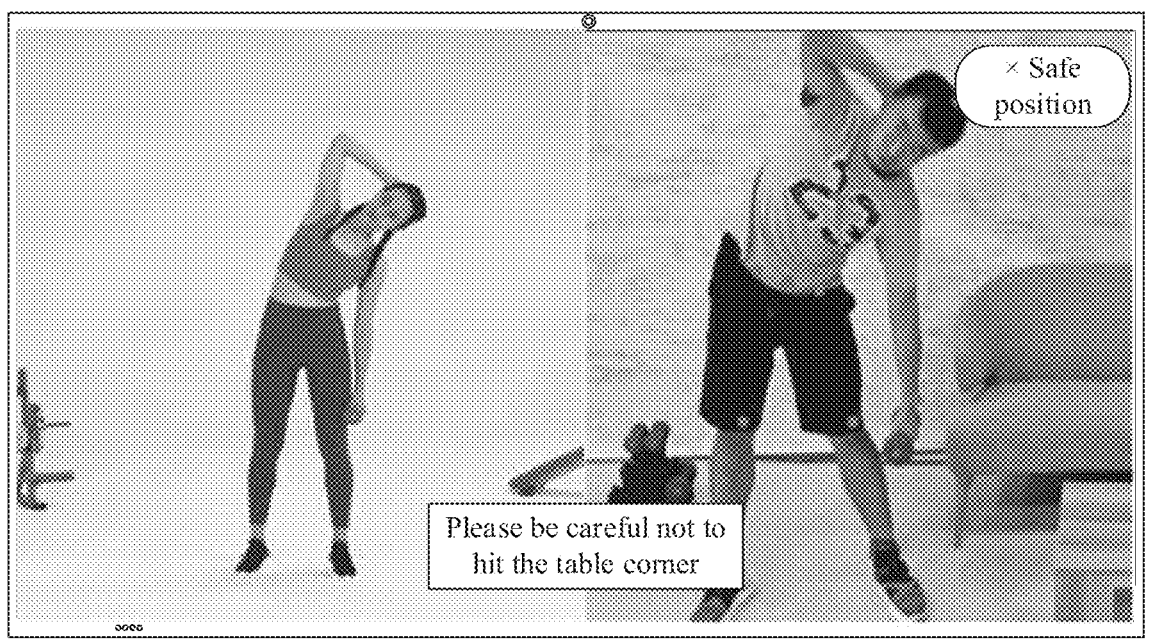
FIG. 7C is a schematic diagram of another voice prompt and interface display effect according to an embodiment of this application.

For example, when the user performs training of dumbbell lateral flexion shown in FIG. 7A, the user has deviated from a range of the screen and the user is next to a table. The electronic device determines that a main flow voice "Please stand in front of the screen" is first triggered, and then a main flow voice "Please keep away from the table corner" is triggered. In this case, referring to FIG. 7B, the electronic device may first play the main flow voice "Please stand in front of the screen", and display first graphic and text information corresponding to the voice. After the electronic device detects that the user stands in front of the screen, referring to FIG. 7C, the electronic device may play the main flow voice "Please keep away from the table corner", and display first graphic and text information corresponding to the voice.

As described above, before the electronic device detects that the user adjusts, according to the main flow voice and the first graphic and text information, to a state required by the first graphic and text information, the first graphic and text information does not disappear, the course does not proceed, and subsequent content of the coach video is not played. Therefore, that the electronic device separately plays each main flow voice neither causes a subsequent course action not to correspond to the voice playing, nor affects timeliness of the voice playing.

In another case, if the electronic device determines, based on a state of the user in a process of performing a same action unit by the user, that at least one main flow voice is triggered, and determines, based on a training action, that at least one non-main flow voice is triggered, because a priority of the main flow voice is high, the electronic device may play the at least one main flow voice and discard the non-main flow voice, to ensure timeliness of the voice playing, ensure that the voice playing matches the training action of the user in real time, and avoid that the user already performs a next action but the electronic device still plays the non-main flow voice of the current action.

For example, the first training action is training of dumbbell lateral flexion, and one training action of dumbbell lateral flexion is an action unit. The second training action is dumbbell pressing, and one dumbbell press is an action unit. When the user performs the first training action, the electronic device determines that a main flow voice "Please keep away from the table corner" and an action improvement voice "Get the lateral flexion range a little bigger" are triggered. In this case, because a priority of the main flow voice is high, the electronic device may play the main flow voice "Please keep away from the table corner" and discard the non-main flow voice. Otherwise, if the electronic device plays both of the triggered voices corresponding to the first training action, when the second training action is performed, playing of a voice corresponding to the first training action may not be completed. As a result, the voice playing does not match the training action, and timeliness of the voice playing is poor.

In another case, in a process of performing a same action unit by the user, the electronic device determines, based on a training action of the user, that a plurality of non-main flow voices are triggered. For this case, in a solution 1, if the priority assignment manner 1 is used, the plurality of non-main flow voices correspond to a same priority, the electronic device may select the first triggered non-main flow voice from the plurality of non-main flow voices for playing. Alternatively, the electronic device may randomly select a non-main flow voice from the plurality of non-main flow voice for playing.

In some embodiments, if the non-main flow voice selected by the electronic device is an action improvement voice, the electronic device may further display second graphic and text information on the screen. The second graphic and text information is graphic and text information of the action improvement voice. For example, the electronic device may display the second graphic and text information on the side where the image of the user is displayed.

Figure 8A:
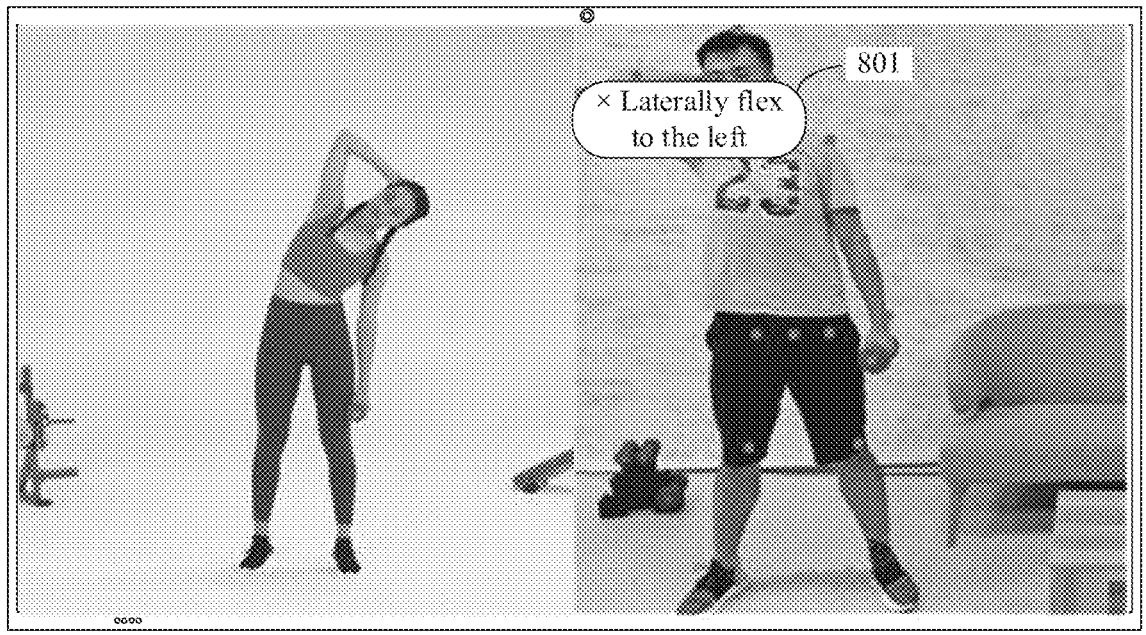
FIG. 8A is a schematic diagram of another voice prompt and interface display effect according to an embodiment of this application.

The second graphic and text information may be a more concise graphic and text representation in the form of the task card. For example, one training action of dumbbell lateral flexion is an action unit, and the electronic device determines that action improvement voices "Please laterally flex to the hand holding the dumbbell" and "A little bigger lateral flexion range can get the external abdominal oblique muscle more excited" are sequentially triggered in a process of performing one training action of dumbbell lateral flexion by the user. The two voices correspond to a same priority. The electronic device may select a voice based on a triggering sequence or randomly for playing. For example, referring to FIG. 8A, the electronic device selects and plays the voice "Please laterally flex to the hand holding the dumbbell", and displays second graphic and text information, that is, prompt information 801, corresponding to the voice on the screen.

Figure 8B:
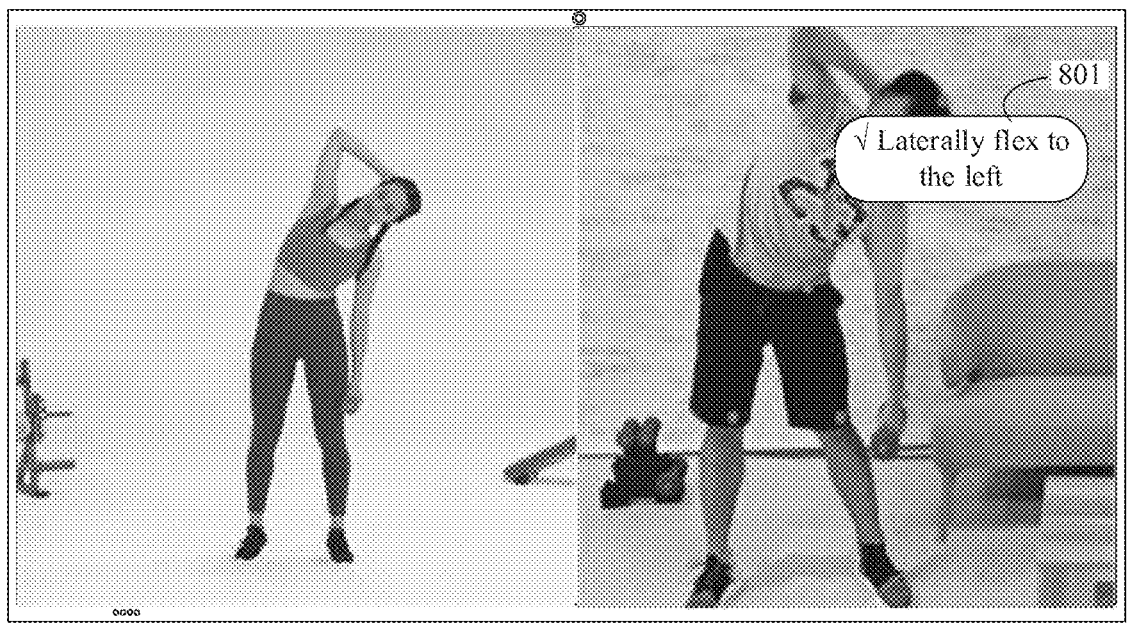
FIG. 8B is a schematic diagram of another interface display effect according to an embodiment of this application.

Similar to the first graphic and text information in the form of the task card, after the electronic device determines that the user adjusts, according to the action improvement voice and the second graphic and text information, the training action of the user to a state required by the second graphic and text information, the second graphic and text information in the form of the task card on the electronic device may be correspondingly changed, to respond to the state adjustment of the user. For example, a completion identifier may be displayed on the second graphic and text information. Then, the second graphic and text information disappears. For example, referring to FIG. 8B, after the electronic device detects that the user laterally flexes to the hand holding the dumbbell, a cross in the prompt information 801 is updated to a check. The check may be the completion identifier. Then, the electronic device stops displaying the prompt information 801.

Figure 8C:
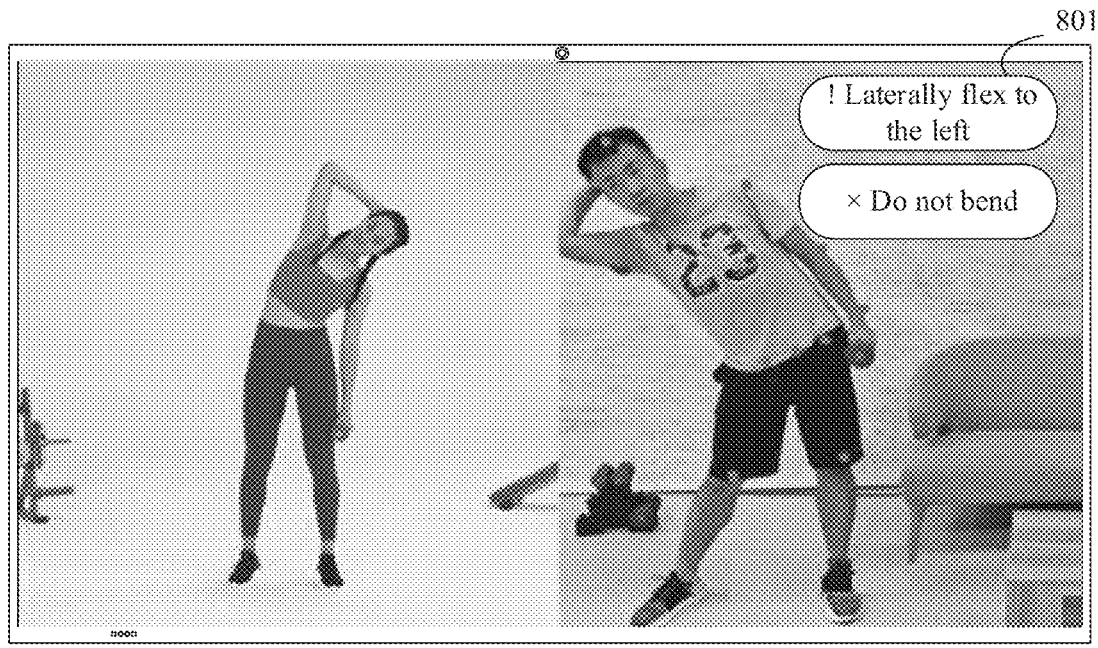
FIG. 8C is a schematic diagram of another voice prompt and interface display effect according to an embodiment of this application.

If the electronic device has not detected, for a long time, that the user the user adjusts, according to the action improvement voice and the second graphic and text information, the training action of the user to the state required by the second graphic and text information, as shown in FIG. 8C, the second graphic and text information is continuously displayed, and the second graphic and text information may be changed correspondingly, to draw attention of the user, and remind the user to focus on content of the second graphic and text information. For example, the electronic device may display a prompt identifier on the second graphic and text information. For example, as shown in FIG. 8C, the cross in the prompt information 801 is updated to an exclamation mark. The exclamation mark may be the prompt identifier. In addition, as a subsequent training action is performed, the electronic device plays a voice "Laterally flex the body, and do not bend forward" for a subsequent action unit. After the second graphic and text information is continuously displayed for a preset duration, or after a training action of a same type ends, the displaying of the second graphic and text information is stopped. That a training action of a same type ends herein means that a training action of this type of dumbbell lateral flexion ends.

It should be noted that, different from the first graphic and text information, when the second graphic and text information is continuously displayed, the course, the training action, and the voice playing are continued, which neither causes the action not to correspond to the voice playing, nor affects timeliness of the voice playing.

In some embodiments, if the non-main flow voice selected by the electronic device is an action improvement voice, and the electronic device has previously played the action improvement voice for a training action of this type of the current fitness training (for example, a plurality of training actions of the same type may be required), the electronic device discards the voice, and reselects a non-main flow voice based on a triggering sequence or randomly for playing. In this way, the electronic device can avoid frequently indicating a same problem of the user and a same improvement requirement. In some technical solutions, when playing the reselected non-main flow voice, the electronic device may further display the second graphic and text information corresponding to the action improvement voice.

For example, one training action of dumbbell lateral flexion is an action unit. In another training action of dumbbell lateral flexion after FIG. 8A (that is, another action unit of a training action of the same type), if a voice selected to be played by the electronic device is the action improvement voice "Please laterally flex to the hand holding the dumbbell", because the electronic device has played the action improvement voice, the electronic device discards the action improvement voice, and reselects a voice for playing.

In some other embodiments, if the non-main flow voice selected by the electronic device is an action improvement voice for a first error (for example, the error is that the user flexes the body to the side of the hand that does not hold a dumbbell), and the electronic device has previously played the action improvement voice for a training action of this type of the current fitness training, the electronic device may play a key action point for the first error, and determine, after the playing of the key action point is completed, whether a voice is triggered for a subsequent training action, to avoid mismatch between the subsequent training action and the voice. When the key point is played, the electronic device may continue to play a coach video of a subsequent course, and the user may continue to perform a subsequent training action. In addition, for different erroneous actions in training actions of a same type, content of corresponding key action points is also different.

For example, one training action of dumbbell lateral flexion is an action unit. In another training action of dumbbell lateral flexion after FIG. 8A, if a voice selected to be played by the electronic device is the action improvement voice "Please laterally flex to the hand holding the dumbbell", because the electronic device has played the action improvement voice, the electronic device does not play the voice, but plays key action points "Get the spine straight and slightly bend over, hold the dumbbell with one hand and place the other hand behind the head, flex the body to the side of the dumbbell, and do not bend forward" of the training action. When the key points are played, the electronic device may continue to play a coach video of a subsequent course, but whether a voice is triggered in a process of performing the subsequent course is not determined temporarily. In some technical solutions, when playing the key action points, the electronic device may further display the second graphic and text information corresponding to the action improvement voice.

In the current fitness training, if a non-main flow voice subsequently selected by the electronic device for an action unit of a training action of this type is still an action improvement voice for the first error, and it is determined that a key action point has been previously played for the first error, the electronic device may discard the action improvement voice, and display second graphic and text information corresponding to the action improvement voice. Then, in some embodiments, the electronic device reselects, from other voices triggered by the action unit, a voice for playing. Alternatively, in some other embodiments, the electronic device does not play a voice triggered by the action unit.

In a solution 2, if the priority assignment manner 2 is used, the electronic device selects a voice with a highest priority for playing. If there are a plurality of voices with the highest priority, a voice is selected based on a triggering sequence or randomly for playing.

In another case, in a process of performing a same action unit by the user, if the electronic device determines, based on a training action of the user, that one non-main flow voice is triggered, the electronic device plays the non-main flow voice.

Figure 9A:
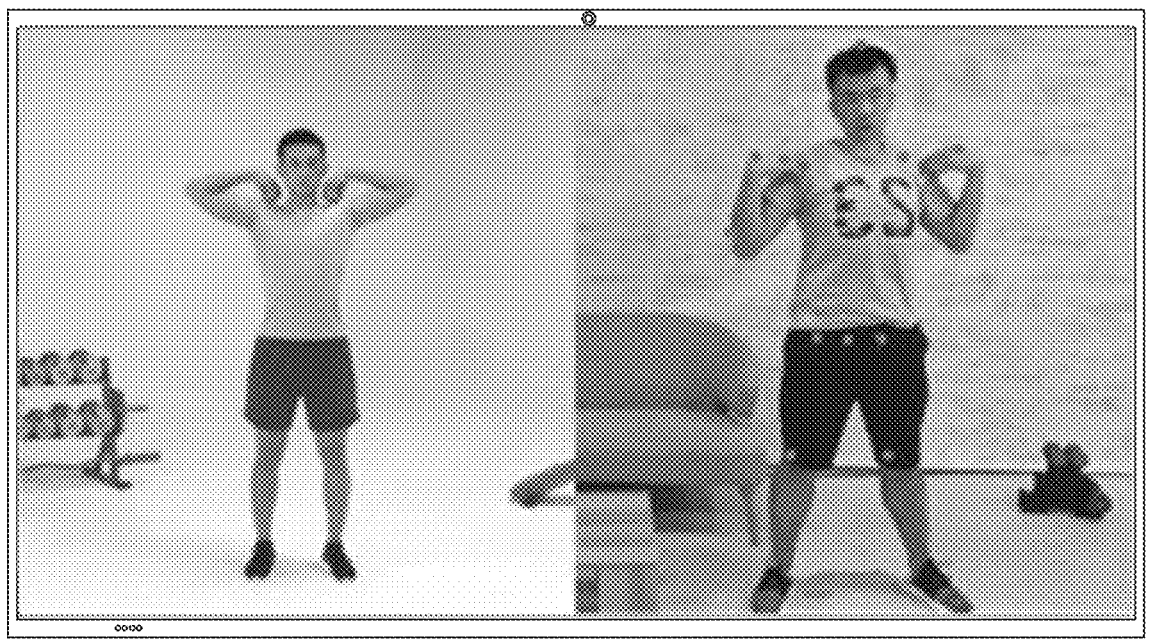
FIG. 9A is a schematic diagram of another interface display effect according to an embodiment of this application.
Figure 9B:
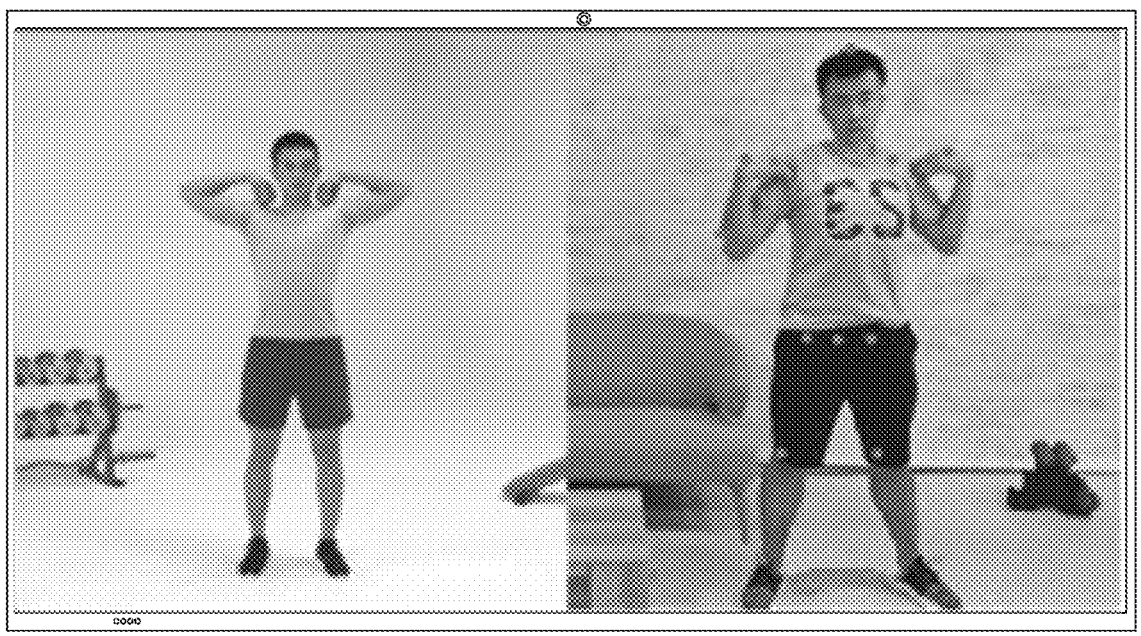
FIG. 9B is a schematic diagram of another voice prompt and interface display effect according to an embodiment of this application.

For example, if the electronic device determines, based on a quantity of training actions of the user in a process of performing a training action of shoulder surrounding shown in FIG. 9A, that a training tempo voice "The last five times, come on" is triggered, referring to FIG. 9B, the electronic device plays the training tempo voice.

In some cases, if the user is performing a training action, and the action is relatively standard, because fewer main flow voices and action improvement voices are triggered, and there are fewer training tempo voices, the electronic device determines that more action evaluation voices are triggered. If the electronic device plays an action evaluation voice for each action, the voice playing is continuously performed, and action evaluation voices are played at an excessive frequent, leading to relatively poor user experience.

In this embodiment of this application, the electronic device may play the action evaluation voices by using a bye mechanism. When the electronic device determines and selects an action evaluation voice from a plurality of voices by using the foregoing solution 1 or solution 2, the electronic device randomly determines whether a current mode is a bye mode or a playing mode. If a result of the random determining by the electronic device is the bye mode, the action evaluation voice is discarded, and the electronic device does not play the action evaluation voice. If the result of the random determining by the electronic device is the playing mode, based on a level (for example, a perfect level or an awesome level) corresponding to a degree of matching between the training action of the user and the standard action, a voice is randomly selected from a corpus including abundant action evaluation voices and played.

In this way, randomness and unpredictability of voice playing can be increased, action evaluation voices can be less repeated, and boredom and predictability of repeated evaluation can be reduced, and the user can be given fresh usage experience.

Figure 10:
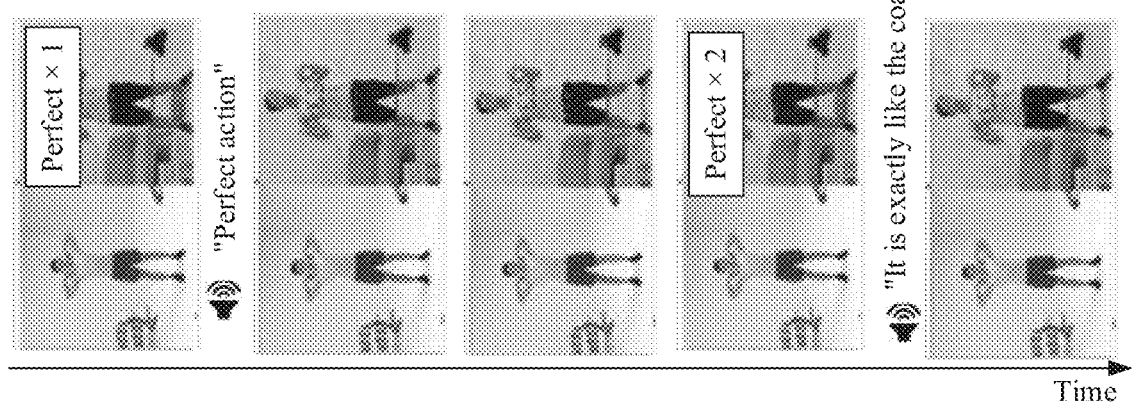
FIG. 10 is a sequence diagram of playing action evaluation voices according to an embodiment of this application.

For example, referring to a sequence diagram shown in FIG. 10, the electronic device may randomly play action evaluation voices at the perfect level in the bye or playing mode. In addition, the action evaluation voices at the perfect level that are played by the electronic device are also randomly determined.

Figure 11:
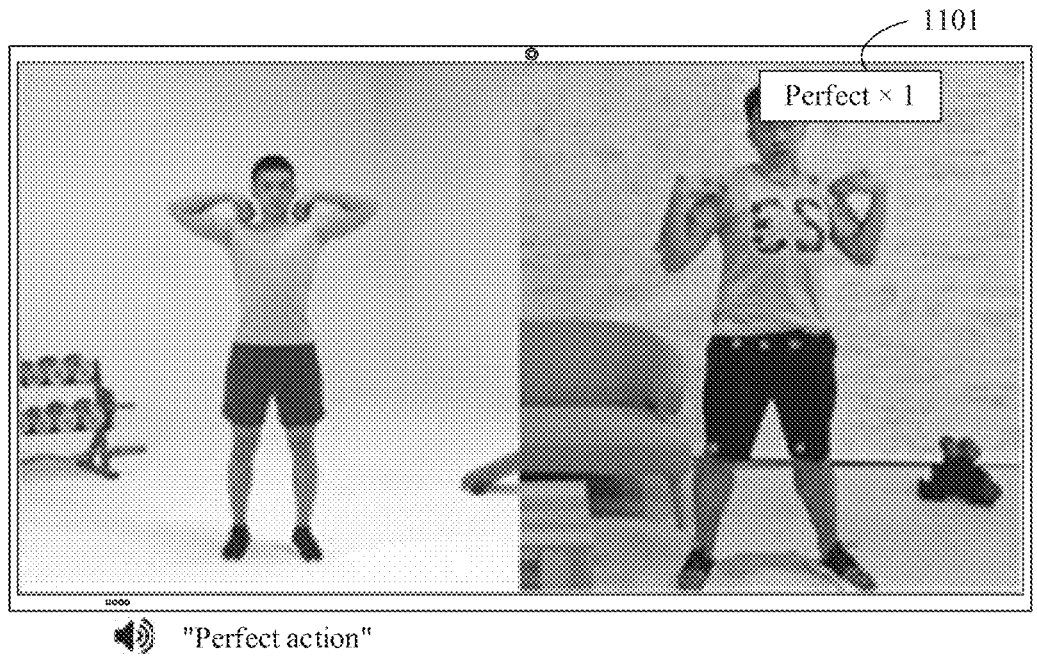
FIG. 11 is a schematic diagram of another voice prompt and interface display effect according to an embodiment of this application.

In some other embodiments, when playing the action evaluation voices, the electronic device may further display graphic and text information corresponding to the action evaluation voices, to better affirm and encourage the user, give confidence to the user, and improve training interest of the user. For example, referring to FIG. 11, when playing an action evaluation voice, the electronic device may further display graphic and text information corresponding to the action evaluation voice, that is, prompt information 1101.

The foregoing description is provided by using an example in which priorities of voices are assigned by using voice types, and the priorities of the voices may alternatively be determined in another manner. For example, the priorities of the voices may be determined based on an actual situation of a user and artificial intelligence AI.

For example, for training actions of a same type, if the electronic device determines, based on an AI learning result, that historical performance of the user is very poor, but a standard degree of a current training action is significantly improved, it may indicate that the user has made a great progress, and therefore the electronic device may preferentially play a positive encouraging action evaluation voice. That is, the action evaluation voice has a highest priority. In this way, the user can learn the progress of the user in time and feel joy of the progress, thereby increasing confidence of the user and increasing interest of the user.

In addition, the electronic device may further adjust the played voice by using AI. For example, it is harder for a fatter user to perform an action of squatting. If a degree of matching between a training action of squatting by the user and a standard action is less than the awesome level but close to the awesome level, the electronic device may play an action evaluation voice at the awesome level to encourage the user. If the degree of matching between the training action of the user and the standard action is close to the perfect level, the electronic device may play an action evaluation voice at the perfect level, to encourage the user and improve confidence of the user.

For another example, if the electronic device determines, based on an AI learning result, that the user has relatively poor endurance, and is likely to stop training halfway, the electronic device may preferentially play a training tempo voice, and increase a playing frequency of the training tempo voice, to help the user learn a current training progress and a quantity of remaining actions in time, and encourage the user to stick with a full set of training actions.

Figure 12:
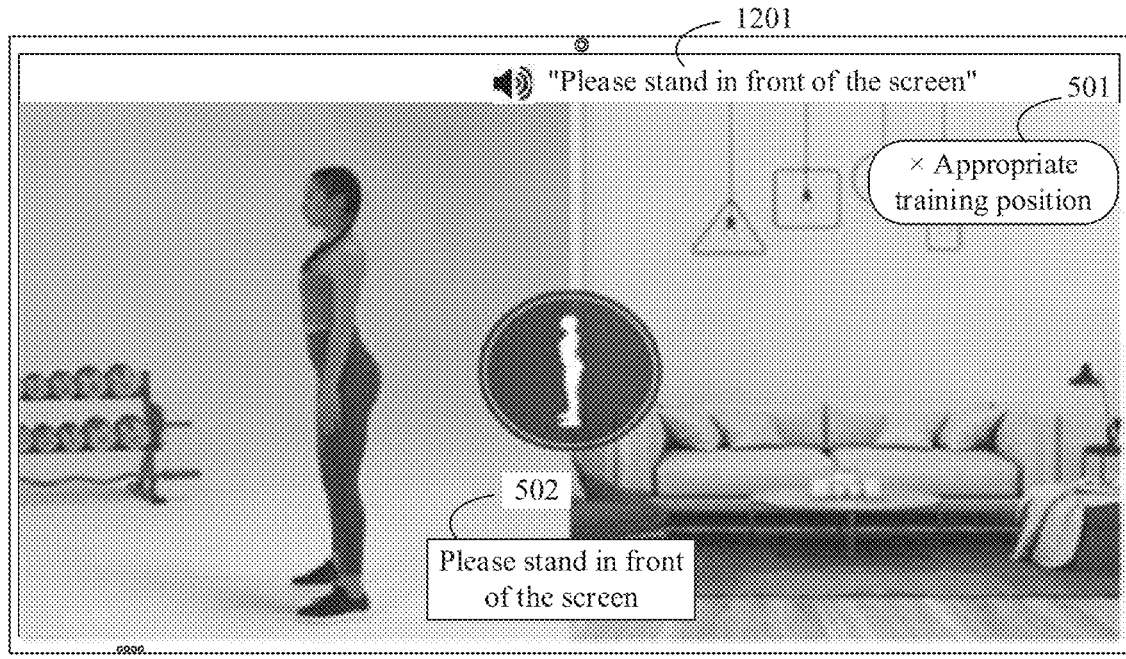
FIG. 12 is a schematic diagram of another interface display effect according to an embodiment of this application.

In some other embodiments, when playing the main flow voice, the action improvement voice, the action evaluation voice, or the training tempo voice, the electronic device may further display, on the screen, text content corresponding to the voice, to help the user more clearly understand voice prompt content of the electronic device. For example, in the case shown in FIG. 5A, referring to FIG. 12, the electronic device may display, on the top of the screen, text content 1201 corresponding to the voice.

In the solution described in the foregoing embodiment, a voice library that includes a plurality of voices of various types and various dimensions is preset on the electronic device. When the user performs exercise training according to a coach video, the electronic device may select, for a current exercise state and exercise action of the user, different voices from the voice library in real time for playing.

In some other embodiments, a single-character corpus instead of a voice library including a plurality of voices is preset on the electronic device. The single-character corpus includes a plurality of single words or phrases. When the user performs exercise training according to a coach video, the electronic device may synthesize, in real time through big data analysis, a more targeted and humanized voice prompt for a current exercise state and exercise action of the user, to perform voice playing.

For example, the single-word/phrase corpus includes "pretty, perfect, awesome, invincible, you, yourself, screen, temperament, front, lateral, flex, are, exactly like, very, quite, of, well, fit, and . . . ". For example, the electronic device synthesizes a voice "You are awesome!" in real time. For another example, the electronic device synthesizes a voice "Pretty, it fits your temperament very well!" in real time.

Figure 13:
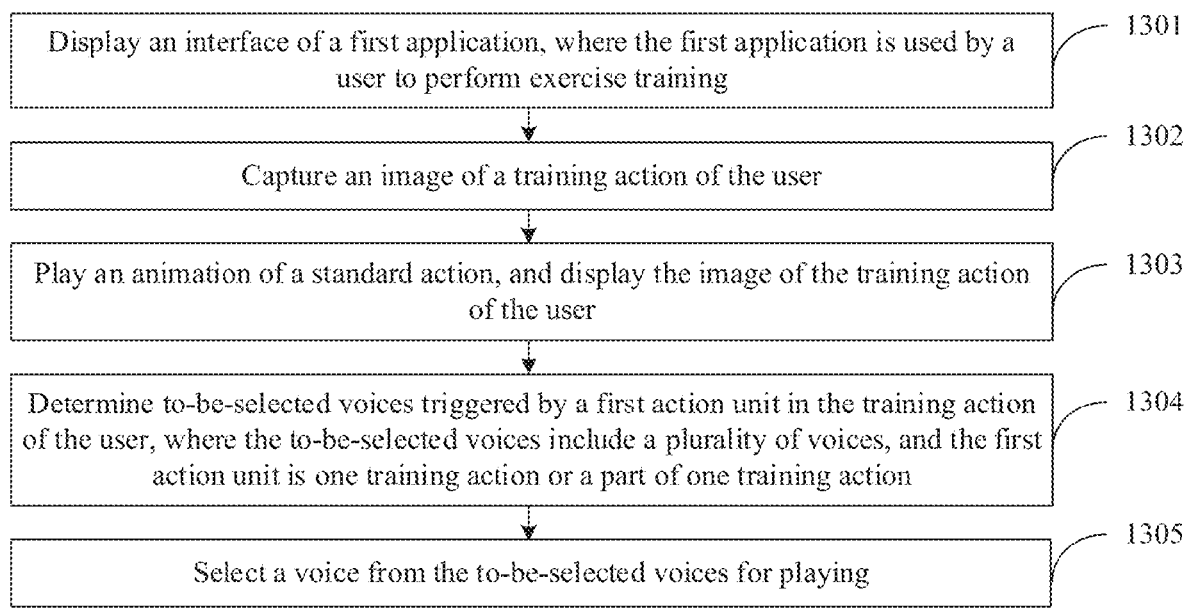
FIG. 13 is another flowchart of voice playing according to an embodiment of this application.

Another embodiment of this application further provides an intelligent voice playing method, which may be applied to an electronic device. The electronic device may include a screen, a camera, and an audio player. Referring to FIG. 13, the method may include the following steps.

1301. The electronic device displays an interface of a first application. The first application is used by a user to perform exercise training.

The electronic device may display the interface of the first application on the screen. For example, the first application may be the AI fitness APP, and the interface of the first application may be the interface shown in FIG. 4(c).

For example, the exercise training may be AI fitness training, AI yoga training, AI bodybuilding operation training, AI somatosensory game, or other exercise training.

1302. The electronic device captures an image of a training action of the user.

The electronic device may capture the image of the training action of the user by using the camera.

1303. The electronic device plays an video of a standard action, and displays the image of the training action of the user.

Figure 6:
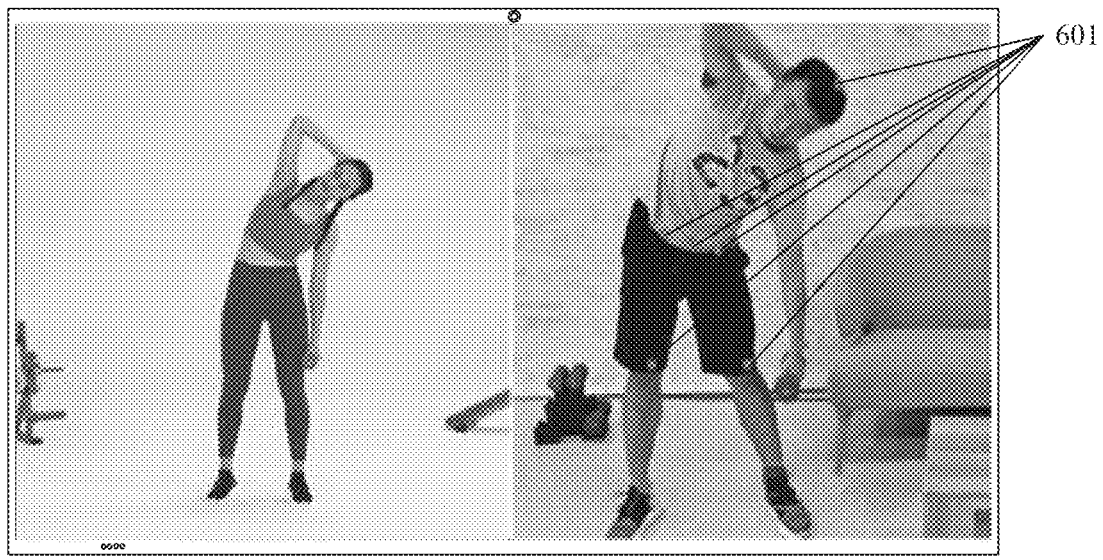
FIG. 6 is a schematic diagram of another interface display effect according to an embodiment of this application.

For example, for an interface in which the electronic device plays the video of the standard action, and displays the image of the training action of the user, refer to FIG. 6.

1304. The electronic device determines to-be-selected voices triggered by a first action unit in the training action of the user. The to-be-selected voices include a plurality of voices, and the first action unit is one training action or a part of one training action.

The first action unit may be any action unit in the exercise training process of the user.

1305. The electronic device selects a voice from the to-be-selected voices for playing.

For related descriptions of step 1304 and step 1305, refer to descriptions of step 305 to step 310. Details are not described herein.

In this way, in the solution described in step 1301 to step 1305, the electronic device can determine, in real time for a current action unit of the user, a plurality of to-be-selected voices that match an exercise state of the user, and select different voices from the to-be-selected voices for playing, to provide real-time voice feedback to the user. In addition, played voice content is abundant and diversified and not easily repeated, and user experience is relatively good.

Another embodiment of this application further provides an electronic device, which may include a display unit, a capture unit, a determining unit, a playing unit, and the like. These units may perform the steps in the foregoing embodiments, to implement the intelligent voice playing method.

In addition, an embodiment of this application further provides an electronic device, including one or more processors, a memory, and one or more computer programs. The one or more computer programs are stored in the memory, and the one or more computer programs include instructions. When the instructions are executed by the one or more processors, the electronic device is enabled to perform the steps in the foregoing embodiments, to implement the intelligent voice playing method.

An embodiment of this application further provides a computer storage medium. The computer storage medium stores computer instructions. When the computer instructions are run on an electronic device, the electronic device is enabled to perform the foregoing related method steps to implement the intelligent voice playing method in the foregoing embodiment.

An embodiment of this application further provides a computer program product. When the computer program product runs on a computer, the computer is enabled to perform the foregoing related method steps to implement the intelligent voice playing method performed by the electronic device in the foregoing embodiment.

In addition, an embodiment of this application further provides an apparatus. The apparatus may be specifically a chip, a component, or a module. The apparatus may include a processor and a memory that are connected. The memory is configured to store computer-executable instructions. When the apparatus runs, the processor may execute the computer-executable instructions stored in the memory, to enable the chip to perform the intelligent voice playing method performed by the electronic device in the foregoing embodiment.

The electronic device, the computer storage medium, the computer program product, and the chip provided in the embodiments are all configured to perform a corresponding method provided above. Therefore, for beneficial effects that can be achieved by the electronic device, the computer storage medium, the computer program product, or the chip, refer to beneficial effects of the corresponding method provided above. Details are not described herein again.

The foregoing descriptions about implementations allow a person skilled in the art to understand that, for convenient and brief description, division into the foregoing function modules is taken as an example for illustration. In actual application, the foregoing functions can be allocated to different function modules and implemented based on a requirement, in other words, an inner structure of an apparatus is divided into different function modules to implement all or some of the functions described above.

In the several embodiments provided in this application, it should be understood that the disclosed apparatuses and methods may be implemented in other manners. For example, the described apparatus embodiments are merely examples. For example, division into the modules or units is merely logical function division, and may be other division during actual implementation. For example, a plurality of units or components may be combined or may be integrated into another apparatus, or some features may be ignored or not performed. In addition, the displayed or discussed mutual couplings or direct couplings or communication connections may be implemented through some interfaces. The indirect couplings or communication connections between the apparatuses or units may be implemented in an electrical form, a mechanical form, or another form.

The units described as separate components may or may not be physically separate, and components displayed as units may be one or more physical units, that is, may be located in one place, or may be distributed on a plurality of different places. Some or all of the units may be selected based on actual requirements to achieve the objectives of the solutions in the embodiments.

In addition, function units in the embodiments of this application may be integrated into one processing unit, or each of the units may exist alone physically, or two or more units may be integrated into one unit. The integrated unit may be implemented in a form of hardware, or may be implemented in a form of a software function unit.

When the integrated unit is implemented in the form of a software function unit and sold or used as an independent product, the integrated unit may be stored in a readable storage medium Based on such an understanding, the technical solutions of the embodiments of this application essentially, or the part contributing to the conventional technology, or all or some of the technical solutions may be implemented in a form of a software product. The software product is stored in a storage medium and includes several instructions for instructing a device (which may be a single-chip microcomputer, a chip, or the like) or a processor (processor) to perform all or some of the steps of the methods in the embodiments of this application. The foregoing storage medium includes any medium that can store program code, such as a USB flash drive, a removable hard disk, a read-only memory (read-only memory, ROM), a random access memory (random access memory. RAM), a magnetic disk, or an optical disc.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A method, comprising:
   displaying, on a display of an electronic device, an interface of a first application associated with exercise training of a user;
   capturing, using a camera of the electronic device, an image of a training action of the user;
   playing, on the display of the electronic device and based on the image of the training action of the user, a video of a standard action related to the training action, wherein the training action comprises a first action unit, and wherein the first action unit comprises the training action or a part of the training action;
   displaying, on the display of the electronic device, the image;
   identifying, by one or more processors of the electronic device and based on the first action unit in the training action, to-be-selected voices;
   selecting, by the one or more processors of the electronic device using Artificial Intelligence (AI), a voice from the to-be-selected voices for playing;
   stopping, on the display of the electronic device, playing the video;
   displaying, on the display of the electronic device, graphic or text information corresponding to the voice;
   detecting, using the camera of the electronic device, that the user has adjusted to a state corresponding to the graphic or text information;
   displaying, on the display of the electronic device and in response to detecting that the user has adjusted to a state, a completion identifier on the graphic and text information;
   stopping displaying, on the display of the electronic device, the graphic and text information; and resuming playing, on the display of the electronic device, the video.

2. The method of claim 1, wherein the to-be-selected voices comprise:
a main flow voice enabling the exercise training to be normally performed, wherein the main flow voice is a high-priority voice; and
at least one non-main flow voice comprising one or more of an action improvement voice, an action evaluation voice, or a training tempo voice, wherein the at least one non-main flow voice is a low-priority voice, and
wherein the method further comprises further selecting the voice for playing based on priorities of the to-be-selected voices.

3. The method of claim 2, wherein the to-be-selected voices further comprise at least one high-priority main flow voice, and wherein the method further comprises separately playing each of the at least one high-priority main flow voice in the to-be-selected voices.

4. The method of claim 3, wherein while separately playing each of the at least one high-priority main flow voice, the method further comprises:
stopping playing the video;
displaying first graphic and text information corresponding to each of the at least one high-priority main flow voice;
detecting that the user has adjusted to a first state corresponding to the first graphic and text information;
displaying a first completion identifier on the first graphic and text information;
stopping displaying the first graphic and text information; and
resuming playing the video.

5. The method of claim 2, wherein the to-be-selected voices further comprise a plurality of low-priority non-main flow voices, and wherein the method further comprises:
selecting a first target voice from the low-priority non-main flow voices; and
playing the first target voice.

6. The method of claim 5, wherein the first target voice is a first triggered voice in the low-priority non-main flow voices.

7. The method of claim 5, wherein the first target voice is a first action improvement voice for a first error in the first action unit, and wherein the method further comprises:
playing the first action improvement voice when the electronic device has not played, in a current exercise training, the first action improvement voice for the training action to which the first action unit belongs; and
when the electronic device has played, in the current exercise training, the first action improvement voice for the training to which the first action unit belongs:
playing a key action point for the first error; or
selecting for playing a second target voice from the low-priority non-main flow voices other than the first action improvement voice.

8. The method of claim 7, wherein while playing the first action improvement voice, the method further comprises:
displaying second graphic and text information corresponding to the first action improvement voice;
detecting that the user has adjusted the training action to a first state corresponding to the second graphic and text information;
displaying a first completion identifier on the second graphic and text information; and
stopping displaying the second graphic and text information.

9. The method of claim 5, wherein the first target voice is a first action evaluation voice, and wherein the method further comprises:
playing the first action evaluation voice when a current mode is a first mode; and
skipping playing the first action evaluation voice when the electronic device identifies randomly that the current mode is a second mode from the modes.

10. The method of claim 9, wherein the at least one non-main flow voice comprises a plurality of levels of action evaluation voices, wherein the first action evaluation voice is at a first level of the levels of the action evaluation voices, and wherein the method further comprises randomly selecting, from the action evaluation voices, voices the first action evaluation voice at the first level for playing.

11. The method of claim 5, further comprising:
playing the first target voice when playing a second voice triggered by another action unit before the first action unit is completed; and
skipping playing the first target voice when playing the second voice triggered by the other action unit before the first action unit is not completed.

12. The method of claim 2, wherein after displaying the interface and before identifying the to-be-selected voices, the method further comprises:
identifying, based on a progress of the exercise training or a first state of the user, that the main flow voice is triggered; and
playing, in response to identifying that the main flow voice is triggered, the main flow voice.

13. The method of claim 2, wherein the action improvement voice guides the user to improve the training action, wherein the action evaluation voice evaluates the user for the training action, and wherein the training tempo voice prompts the user of a progress of the exercise training.

14. The method of claim 1, further comprising:
obtaining a first image comprising the first action unit;
playing a first audio when the first image meets a first condition;
obtaining a second image comprising a second action of the user; and
playing a second audio when the second image meets the first condition, wherein the second audio is different from the first audio.

15. The method of claim 14, further comprising:
identifying a first action feature based on the first image;
identifying a second action feature based on the second image;
identifying that the first image meets the first condition when a first match degree of the first action feature and a third action feature is greater than or equal to a first threshold, wherein the third action feature is of a first preset action corresponding to the first action unit; and
identifying that the second image meets the first condition when a second match degree of the second action feature and a fourth action feature is greater than or equal to the first threshold, wherein the fourth action feature is of a second preset action corresponding to the second action.

16. The method of claim 14, further comprising:
displaying first information corresponding to the first audio while playing the first audio; and
displaying second information corresponding to the second audio while playing the second audio.

17. The method of claim 14, further comprising
displaying the first image after obtaining the first image;
displaying the second image after obtaining the second image; and
displaying a preset video while displaying the first image and the second image.

18. The method of claim 14, further comprising:
identifying a first audio group when the first image meets the first condition, wherein the first audio group comprises the first audio;
selecting the first audio from the first audio group;
identifying the first audio group when the second image meets the first condition, wherein the first audio group comprises the second audio;
selecting the second audio from the first audio group;
selecting the first audio from the first audio group according to a first priority of the first audio; and
selecting the second audio from the first audio group according to a second priority of the second audio.

19. A computer program product comprising computer-executable instructions that are stored on a non-transitory computer-readable medium and that, when executed by one or more processors, cause an electronic device to:
display, on a display of the electronic device, an interface of a first application associated with exercise training of a user;
capture, using a camera of the electronic device, an image of a training action of the user;
play, on the display of the electronic device and based on the image of the training action of the user, a video of a standard action related to the training action, wherein the training action comprises a first action unit, and wherein the first action unit comprises the training action or a part of the training action;
display, on the display of the electronic device, the image;
identify, by the one or more processors of the electronic device and based on the first action unit in the training action, to-be-selected voices;
select, by the one or more processors of the electronic device using Artificial Intelligence (AI), a voice from the to-be-selected voices for playing;
stop, on the display of the electronic device, playing the video;
display, on the display of the electronic device, graphic or text information corresponding to voice;
detect, using the camera of the electronic device, that the user has adjusted to a state corresponding to the graphic or text information;
display, on the display of the electronic device and in response to detecting that the user has adjusted to a state, a completion identifier on the graphic and text information;
stop displaying, on the display of the electronic device, the graphic and text information; and
resume playing, on the display of the electronic device, the video.

20. An electronic device, comprising:
a memory configured to store instructions; and
one or more processors coupled to the memory and configured to execute the instructions to:
display, on a display of the electronic device, an interface of a first application associated with exercise training of a user;
capture, using a camera of the electronic device, an image of a training action of the user;
play, on the display of the electronic device and based on the image of the training action of the user, a video of a standard action related to the training action, wherein the training action comprises a first action unit, and wherein the first action unit comprises the training action or a part of the training action;
display, on the display of the electronic device, the image;
identify, by the one or more processors of the electronic device and based on the first action unit in the training action, to-be-selected voices;
select, by the one or more processors of the electronic device using Artificial Intelligence (AI), a voice from the to-be-selected voices for playing;
stop, on the display of the electronic device, playing the video;
display, on the display of the electronic device, graphic or text information corresponding to voice;
detect, using the camera of the electronic device, that the user has adjusted to a state corresponding to the graphic or text information;
display, on the display of the electronic device and in response to detecting that the user has adjusted to a state, a completion identifier on the graphic and text information;
stop displaying, on the display of the electronic device, the graphic and text information; and
resume playing, on the display of the electronic device, the video.

\* \* \* \* \*

UNITED STATES PATENT AND TRADEMARK OFFICE
CERTIFICATE OF CORRECTION

| | | |
|---|---|---|
| PATENT NO. | : 12,070,673 B2 | |
| APPLICATION NO. | : 17/634601 | |
| DATED | : August 27, 2024 | |
| INVENTOR(S) | : Xindi Yu and Hang Liu | |

It is certified that error appears in the above-identified patent and that said Letters Patent is hereby corrected as shown below:

In the Claims

Claim 10, Column 30, Line 16: "evaluation voices, voices the first" should read "evaluation voices, the first"

Signed and Sealed this
First Day of October, 2024

Katherine Kelly Vidal
*Director of the United States Patent and Trademark Office*